United States Patent
Guadiuso et al.

(10) Patent No.: US 12,055,495 B2
(45) Date of Patent: Aug. 6, 2024

(54) DIAGNOSIS OF DISEASE USING LASER-INDUCED BREAKDOWN SPECTROSCOPY AND MACHINE LEARNING

(71) Applicants: University of Massachusetts, Boston, MA (US); The United States Government as Represented by the Department of Veterans Affairs, Washington, DC (US)

(72) Inventors: Rosalba Guadiuso, Mola di Bari (IT); Noureddine Melikechi, Westford, MA (US); Weiming Xia, Boston, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 307 days.

(21) Appl. No.: 17/305,901

(22) Filed: Jul. 16, 2021

(65) Prior Publication Data
US 2022/0018784 A1 Jan. 20, 2022

Related U.S. Application Data

(60) Provisional application No. 63/201,470, filed on Apr. 30, 2021, provisional application No. 62/705,816, filed on Jul. 16, 2020.

(51) Int. Cl.
*G01N 21/71* (2006.01)
*G01N 33/487* (2006.01)
(Continued)

(52) U.S. Cl.
CPC ......... *G01N 21/718* (2013.01); *G01N 33/487* (2013.01); *G06N 5/022* (2013.01);
(Continued)

(58) Field of Classification Search
CPC ..... G01N 21/718; G01N 33/487; G06N 5/022
See application file for complete search history.

(56) References Cited

U.S. PATENT DOCUMENTS

| 5,991,653 A | 11/1999 | Richards-Kortum et al. |
| 6,789,069 B1 | 9/2004 | Barnhill et al. |
(Continued)

FOREIGN PATENT DOCUMENTS

JP 2014044110 A 3/2014

OTHER PUBLICATIONS

Adlard, et al., "Metals and Alzheimer's Disease: How Far Have We Come in the Clinic?", Journal of Alzheimer's Disease, vol. 62, 2018, pp. 1369-1379.
(Continued)

*Primary Examiner* — Michael A Lyons
(74) *Attorney, Agent, or Firm* — Brake Hughes Bellermann LLP

(57) ABSTRACT

Diagnosing a pathology using LIBS and biological fluids includes focusing light on to a sample on a substrate to cause ablation of the sample and formation of a plasma, collecting optical emission from the plasma, and providing the optical emission to a spectroscopic acquisition component that provides information on spectral data of the plasma. The spectral data is provided to a machine learning algorithm to diagnose a pathology in the sample, where the algorithm is trained on a training set that includes spectral features in a difference spectrum derived from differences between a first LIBS optical emission spectrum collected from one or more samples of the biological fluid that have the pathology or known progress of the pathology and a second LIBS optical emission spectrum collected from one or more samples of the predetermined biological fluid that do not have the pathology or the known progress of the pathology.

18 Claims, 18 Drawing Sheets

(51) Int. Cl.
*G06N 5/022* (2023.01)
*G16H 10/40* (2018.01)
*G16H 50/20* (2018.01)

(52) U.S. Cl.
CPC .............. *G16H 10/40* (2018.01); *G16H 50/20* (2018.01); *G01N 2201/129* (2013.01)

(56) References Cited

U.S. PATENT DOCUMENTS

| | | | |
|---|---|---|---|
| 7,394,537 | B1 | 7/2008 | Lindfors et al. |
| 7,899,625 | B2 | 3/2011 | Bhanot et al. |
| 8,450,057 | B2 | 5/2013 | Gordon et al. |
| 10,506,985 | B2 * | 12/2019 | Gaudiuso ............. G01N 21/718 |
| 2003/0218747 | A1 | 11/2003 | Ramaseder et al. |
| 2004/0199079 | A1 | 10/2004 | Chuck et al. |
| 2016/0116416 | A1 | 4/2016 | Wang et al. |
| 2018/0120205 | A1 | 5/2018 | Melikechi |
| 2018/0360390 | A1 * | 12/2018 | Gaudiuso ............. A61B 5/4325 |
| 2019/0267221 | A1 * | 8/2019 | Pringle ............... H01J 49/0036 |
| 2020/0300702 | A1 * | 9/2020 | Pyun ...................... A61B 5/444 |

OTHER PUBLICATIONS

Anabitarte, et al., "Laser-Induced Breakdown Spectroscopy: Fundamentals, Applications, and Challenges", International Scholarly Research Network, ISRN Spectroscopy vol. 2012, Article ID 285240, Sep. 2012, 12 pages.

Baudelet, Matthieu, et al., "Spectral signature of native CN bonds for bacterium detection and identification using femtosecond laser-induced breakdown spectroscopy", Applied Physics Letters, vol. 88(6), 2006, 3 pages.

Chen, et al., "Diagnosis of human malignancies using laser-induced breakdown spectroscopy in combination with chemometric methods", Spectrochimica Acta Part B, vol. 139, 2018, pp. 63-69.

Chen, et al., "Discrimination of lymphoma using laser-induced breakdown spectroscopy conducted on whole blood samples", Biomedical Optics Express, vol. 9, Issue 3, Mar. 2018, pp. 1057-1068.

Cruz, et al., "Applications of Machine Learning in Cancer Prediction and Prognosis", Cancer Informatics, vol. 2, Jan. 2006, pp. 59-78.

El Haddad, et al., "Good practices in LIBS analysis: Review and advices", Spectrochimica Acta Part B: Atomic Spectroscopy, vol. 101, Nov. 2014, pp. 171-182.

Friedman, "Greedy function approximation: A gradient boosting machine", IMS 1999 Reitz Lecture (https://statweb.stanford.edu/~jhf/ftp/trebst.pdf), Feb. 1999, 39 pages.

Gaudiuso, et al., "Laser-induced breakdown spectroscopy for human and animal health: a review", Spectrochim. Acta B, vol. 152, 2019, pp. 123-148.

Gaudiuso, et al., "Using LIBS to diagnose melanoma in biomedical fluids deposited on solid substrates: Limits of direct spectral analysis and capability of machine learning", Spectrochimica Acta Part B: Atomic Spectroscopy, vol. 146, Aug. 2018, pp. 106-114.

Huang, et al., "Raman Spectrometric Detection Methods for Early and Non-Invasive Diagnosis of Alzheimer's Disease", J Alzheimers Dis., vol. 57(4), 2017, pp. 1145-1156.

Jack, et al., "A/T/N: an unbiased descriptive classification scheme for Alzheimer disease biomarkers", Neurology, vol. 37, Aug. 2016, pp. 539-547.

Markushin, et al., "Tag-femtosecond laser-induced breakdown spectroscopy for the sensitive detection of cancer antigen 125 in blood plasma", Anal Bioanal Chem, vol. 407(7), Mar. 2015, pp. 1849-1855.

Melikechi, et al., "Age-specific discrimination of blood plasma samples of healthy and ovarian cancer prone mice using laser-induced breakdown spectroscopy", Spectrochimica Acta Part B: Atomic Spectroscopy, vol. 123, pp. 33-41, Sep. 2016, pp. 33-41.

Olsson, et al., "CSF and blood biomarkers for the diagnosis of Alzheimer's disease: a systematic review and meta-analysis", The Lancet Neurology, vol. 15, No. 7, Jun. 2016, pp. 673-684.

Pedregosa, et al., "Scikit-learn: Machine Learning in Python", Journal of Machine Learning Research, vol. 12, 2011, pp. 2825-2830.

Pohjalainen, et al., "Feature Selection Methods and Their Combinations in High-Dimensional Classification of Speaker Likability, Intelligibility and Personality Traits", Computer Speech & Language, vol. 29, Issue 1, Jan. 2013, 21 pages.

Pokrajac, et al., "Automatic classification of laser-induced breakdown spectroscopy (LIBS) data of protein biomarker solutions", Appl Spectrosc, vol. 68(9), 2014, pp. 1067-1075.

Pořízka, et al., "On the utilization of principal component analysis in laser-induced breakdown spectroscopy data analysis, a review", Spectrochimica Acta Part B: Atomic Spectroscopy, vol. 148,, Oct. 2018, pp. 65-82.

Sivakumar, et al., "An experimental observation of the different behavior of ionic and neutral lines of iron as a function of number density in a binary carbon-iron mixture", Spectrochimica Acta Part B: Atomic Spectroscopy, vol. 82, Apr. 2013, pp. 76-82.

Sivakumar, et al., "Detection and classification of live and dead *escherichia coli* by laser-induced breakdown spectroscopy", Astrobiology, vol. 15, 2015, pp. 144-153.

Stanevski, et al., "Using Support Vector Machine as a Binary Classifier", International Conference on Computer Systems and Technologies—CompSysTech, 2005, 5 pages.

Tharwat, et al., "Linear discriminant analysis: A detailed tutorial", AI Communications 00, IOS Press (http://usir.salford.ac.uk/id/eprint/52074/1/AI_Com_LDA_Tarek.pdf), 2017, 22 pages.

Welling, "Fisher Linear Discriminant Analysis", https://www.cs.huji.ac.il/~csip/Fisher-LDA.pdf, 2009, 5 pages.

* cited by examiner

DIAGNOSIS OF DISEASE USING LASER-INDUCED BREAKDOWN SPECTROSCOPY AND MACHINE LEARNING

CROSS REFERENCE TO RELATED APPLICATIONS

This application claims priority to U.S. Provisional Application No. 62/705,816, filed Jul. 16, 2020, and titled "DIAGNOSIS OF DISEASE USING LASER-INDUCED BREAKDOWN SPECTROSCOPY AND MACHINE LEARNING" and to U.S. Provisional Application No. 63/201,470, filed Apr. 30, 2021, and titled "DIAGNOSIS OF GULF WAR ILLNESS USING LASER-INDUCED SPECTRA ACQUIRED FROM PLASMA HUMAN SAMPLES."

TECHNICAL FIELD

This description relates to diagnosis and/or monitoring progress of a pathology and, in particular, to diagnosis of Alzheimer's using laser-induced breakdown spectroscopy and machine learning.

BACKGROUND

It is estimated that, by the year 2050, the number of Alzheimer's disease (AD) cases in the US will exceed 20 million and the related healthcare costs will reach $1 trillion. AD, a neurodegenerative disease characterized by progressive and irreversible cognitive loss, is currently incurable. An efficient management of symptoms, as well as the success of clinical trials of drug candidates, relies on early diagnosis and clear discrimination of AD from other dementias. Three biomarkers, collectively identified as ATN, were defined for AD, i.e., amyloid deposit (A), Tau pathology (T), and neurodegeneration (N). The ATN biomarkers can be detected in living individuals, but since the required procedures are either costly (e.g., brain imaging) or invasive (e.g., lumbar puncture for cerebrospinal fluid harvesting), diagnoses still largely rely on neurological and cognitive symptoms. This approach has two main pitfalls: 1) AD pathophysiological processes may start long before symptoms appear; and 2) symptoms themselves do not allow discriminating AD from other dementias due to their low specificity for AD. Therefore, there is a strong need for non-invasive cost-effective tests for AD early diagnosis.

SUMMARY

Systems and methods for diagnosing or monitoring progress of a pathology using laser induced breakdown spectroscopy (LIBS) and machine learning are disclosed herein below.

In a general aspect, a method for screening patients with, diagnosing, or monitoring progress of a pathology using laser induced breakdown spectroscopy (LIBS) and biological fluids includes depositing a sample of a predetermined biological fluid on a predetermined substrate, focusing light from a laser light source on the sample deposited on the predetermined substrate, where an energy and pulse length of the laser light source are configured to cause ablation of the sample and formation of a plasma, and collecting optical emission from the plasma. The collected optical emission is provided to a spectroscopic acquisition component, where the spectroscopic acquisition component provides information on spectral data of the plasma, and the spectral data from the collected optical emission is provided to a processing component, where the processing component includes one or more processors. A machine learning algorithm and the one or more processors are used to screen a patient with, diagnose, or monitor progress of the pathology in the sample, where the machine learning algorithm is trained on a training set that includes spectral features in a difference spectrum derived from differences between a first LIBS optical emission spectrum collected from one or more samples of the predetermined biological fluid that have the pathology or known progress of the pathology and a second LIBS optical emission spectrum collected from one or more samples of the predetermined biological fluid that do not have the pathology or the known progress of the pathology.

In another general aspect, a system for screening patients with, diagnosing, or monitoring progress of a pathology using laser induced breakdown spectroscopy (LIBS) and biological fluids, using laser induced breakdown spectroscopy (LIBS) and biomedical fluids, includes a substrate configured to have a sample of a predetermined biological fluid deposited on the substrate, a laser light source, an optical subsystem configured to receive light from the laser light source and focus the received light on the sample deposited on the substrate, where the energy and pulse length of the laser light source are configured to cause ablation of the sample and substrate and formation of a plasma, a light collection optical subsystem configured to collect optical emission from the plasma, a spectroscopic acquisition component configured to receive collected optical emission from the light collection optical subsystem and to provide spectral data, the spectroscopic acquisition component including a spectrometer and a detector, and a processing component including one or more processors and configured to receive the spectral data from the spectroscopic acquisition component. The one or more processors are configured to use a machine learning algorithm to screen a patient with, diagnose, or monitor progress of the pathology in the sample, where the machine learning algorithm is trained on a training set that includes spectral features in a difference spectrum derived from differences between a first LIBS optical emission spectrum collected from one or more samples of the predetermined biological fluid that have the pathology or known progress of the pathology and a second LIBS optical emission spectrum collected from one or more samples of the predetermined biological fluid that do not have the pathology or the known progress of the pathology.

Implementations can include one or more features, alone or in any combination with each other.

For example, the predetermined biological fluid can include blood or blood plasma and the pathology can be Alzheimer's disease.

The machine learning algorithm can include a Quadratic Discriminant Analysis (QDA) algorithm.

The spectral features used to train the machine learning algorithm can be weighted based on their ability to correctly classify a sample.

Each spectral feature can be labelled as indicating or contra-indicating the pathology or the known progress of the pathology based on its polarity in the difference spectrum.

The first and second LIBS spectra can be normalized for their total emission intensities.

The spectral features can include only features that are absent in a spectrum of the substrate.

The spectral features can include only features that are absent in a spectrum of the substrate or that, in a spectrum of the substrate, had an intensity lower than 50% of the intensity in the samples' average spectra.

Providing the spectral data from the collected optical emission to a processing component can include generating difference spectra to enhance spectral differences between samples obtained from patients having the pathology and samples obtained from healthy controls.

Using the machine learning algorithm and the one or more processors to screen a patient with the pathology, diagnose the pathology, or monitor progress of the pathology in the sample can include determining polarities of the spectral features when compared to a model difference spectrum and classifying the sample based on the number of positive polarity spectral features compared to the number of negative polarity spectral features.

For a better understanding of the present teachings, together with other and further objects thereof, reference is made to the accompanying drawings and detailed description and its scope will be pointed out in the appended claims.

The details of one or more examples of implementations are set forth in the accompanying drawings and the description below. Other features will be apparent from the description and drawings, and from the claims.

DETAILED DESCRIPTION

Figure 1:
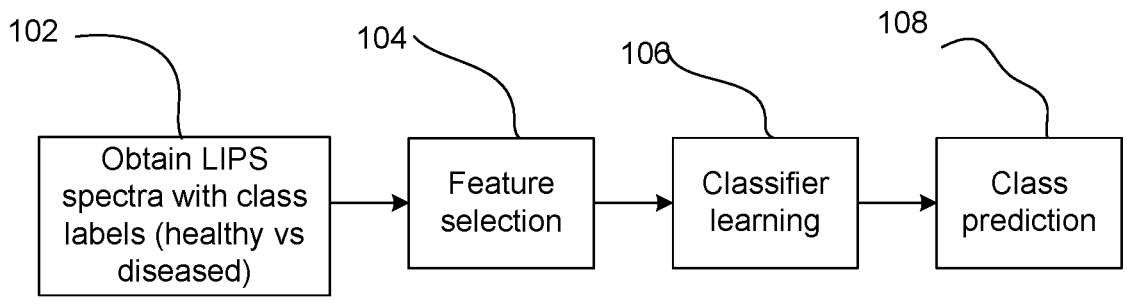
FIG. 1 is a is a flow diagram of one embodiment of the described improvement according to an example implementation.

The following detailed description is not to be taken in a limiting sense but is made merely for the purpose of illustrating the general principles of these teachings, since the scope of these teachings is best defined by the appended claims. Although the teachings have been described with respect to various embodiments, it should be realized these teachings are also capable of a wide variety of further and other embodiments within the spirit and scope of the appended claims.

As used herein, the singular forms "a," "an," and "the" include the plural reference unless the context clearly dictates otherwise.

"Light," as used herein, refers to electromagnetic radiation.

Systems and methods for diagnosing or monitoring progress of a pathology using laser induced breakdown spectroscopy (LIBS) and machine learning are presented herein.

In Laser-Induced Breakdown Spectroscopy (LIBS), optical (i.e., ultraviolet, visible, and/or infrared) emission spectra are obtained from Laser-Induced Plasmas (LIP), i.e., highly ionized gases that can be produced by the interaction of intense laser pulses and matter. LIPs are dynamic systems, that emit ultraviolet, visible, and infrared radiation during their persistence time. This emission constitutes the LIBS signal, and, since the elemental composition of LIPs is the same as the irradiated target, assuming the ablation is stoichiometric, LIBS spectra can be used for qualitative and quantitative analysis of the target itself. Some of the most useful features of LIBS as an analytical technique include: simultaneous analysis of all elements present in the target, irrespective of their atomic mass; possibility of analyzing samples of virtually any chemical nature and state of aggregation; limited or absent sample preparation; immediate response; relatively low cost; and the possibility of in situ and stand-off analyses. For these reasons, LIBS lends itself to a large number of analytical applications, in a variety of diverse fields. Biomedical applications of LIBS are currently in a phase of great vitality. An advantage of TABS over other spectroscopic techniques is that it can be used to interrogate tissues without preparation protocols that select for or inadvertently alter sample constituents or disrupt constituent interactions. This approach does not hypothesize the importance of a single pathway but rather seeks to provide an unbiased survey and assessment of the spectroscopic signatures of all potential biological markers present, and their interactions, in intact tissue.

In some implementations, a minimally invasive approach to medical diagnosis can be used, i.e., LIBS liquid biopsy. Instead of tissues, this method employs easily harvested biological fluids, such as, for example, blood, urine, or saliva, that are deposited and dried on solid substrates prior to laser irradiation. LIBS liquid biopsy makes it intrinsically versatile and applicable to problems of different nature, such as, in the biomedical field, the diagnosis of different diseases. The use of machine learning, moreover, can provide several advantages such as automated procedures; speed of analysis; high classification accuracy; and generation of spectral libraries containing a large number of samples.

The combined use of LIBS and machine learning for the diagnosis of AD using biomedical fluids is proposed herein. Using an elemental analysis technique for diagnosis of AD is justified by the increasing attention that the role of metals in AD onset and progress has been receiving in the past several decades. Despite these efforts, a clear correlation between the blood levels of various metals and AD is yet to be established. As described herein, micro-drops of plasma from a cohort of AD patients and healthy controls (HC) were analyzed and techniques focused on distinguishing the two classes with a data analysis approach based on the use of LIBS difference spectra were developed.

Techniques described herein relate generally to methods and systems for diagnosing or monitoring progress of a pathology and, more particularly, to methods and systems for diagnosing or monitoring progress of a pathology using laser induced breakdown spectroscopy (LIBS) and machine learning.

Outcomes of patients are significantly improved if a pathology is detected early. Early detection can be related to noninvasive monitoring, since patients are more likely to be monitored by noninvasive methods. A "liquid biopsy" provides a noninvasive path for determining an early diagnosis or monitoring progress for pathology.

Using previous techniques, Alzheimer's disease is difficult to detect before typical pathological changes have occurred in the brain. However, some early indicators should be possible. For example, it has been found that the amyloid beta folds incorrectly due to pathological changes. This misfolding may be diagnosed using a blood test, which will allow detection of the disease approximately many years before the first clinical symptoms can be seen. However, according to a recent study, the test only produces true positive results in 71% of the cases and provides false positives in 9% of the cases. See Andreas Nabers, Henning Hafermann, Jens Wiltfang, Klaus Gerwert. Aβ and tau structure-based biomarkers for a blood- and CSF-based two-step recruitment strategy to identify patients with dementia due to Alzheimer's disease. Alzheimer's & Dementia: Diagnosis, Assessment & Disease Monitoring, 2019; 11: 257 DOI: 10.1016/j.dadm.2019.01.008.

Thus, there is a need for a more accurate test for early detection of Alzheimer's disease.

FIG. 1 is flowchart diagram of an embodiment of the techniques descried herein. As shown in FIG. 1, LIPS spectra are obtained from AD samples/patients and from HC samples patents, and the spectra are labelled as AD or HC (102). Salient features of the spectra that can be used for training a machine learning model used to diagnose a pathology can be selected (104). The selection of the salient features can occur before the machine learning model is applied to the obtained LIBS spectra. The samples analyzed can include samples from normal subjects and samples from subjects with Alzheimer's disease. The obtained spectra can be provided to machine learning algorithms/classifiers to train the algorithms/classifiers to recognize spectra from AD and HC samples (106). The algorithms/classifiers can include, for example, Linear Discriminant Analysis (LDA), Quadratic Discriminant Analysis (QDA), Random Forest (RA), Support Vector Machines (SVM), Fisher Discriminant Analysis (FDA), and Gradient Boosting algorithms/classifiers. It should be noted that this list of algorithms/classifiers is not exhaustive, and other machine learning algorithms can be used.

Figure 2:
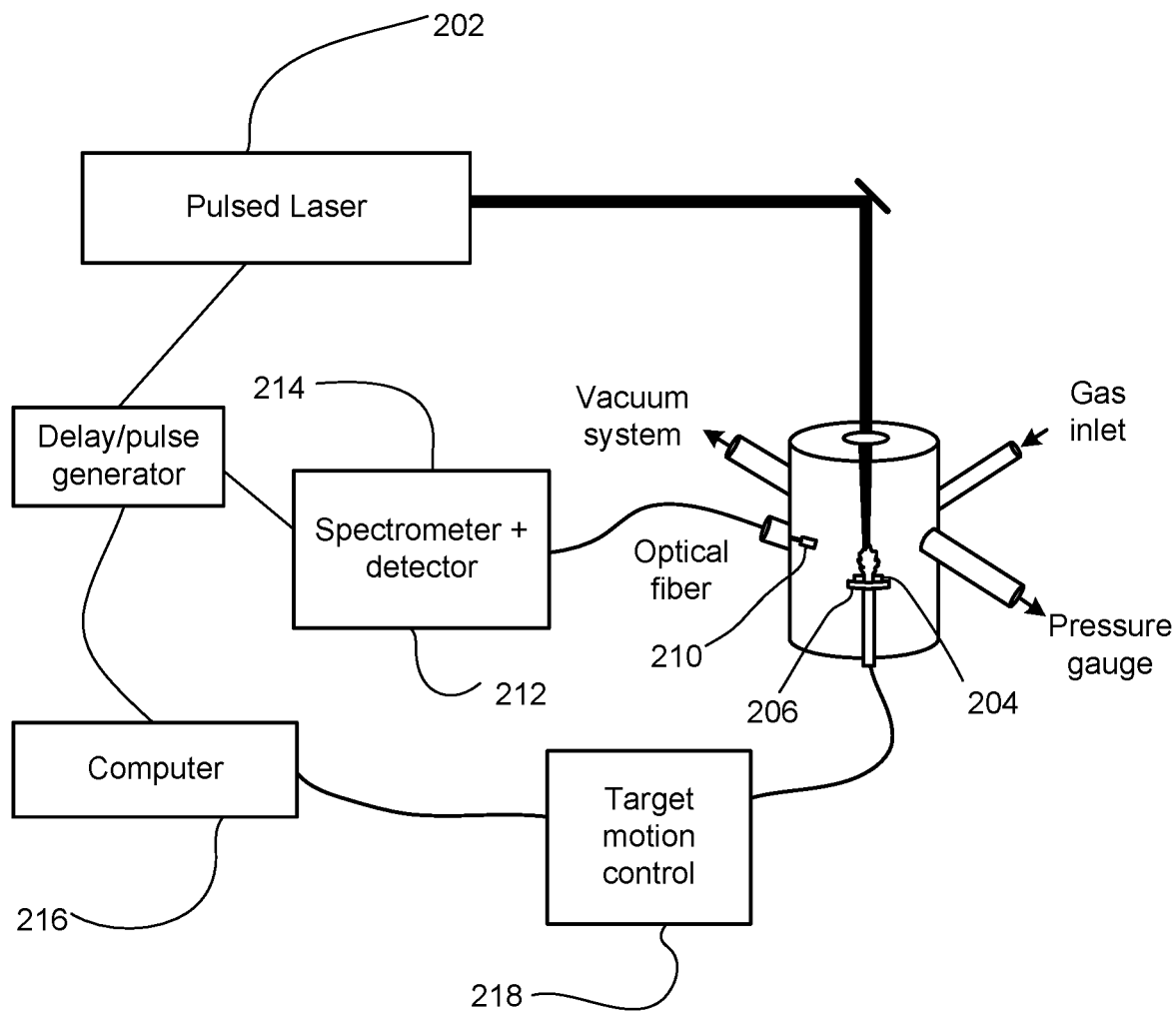
FIG. 2 is a graphical schematic representation of one embodiment of the system according to an example implementation.

FIG. 2 is a schematic diagram of a system 200 for gathering LIBS spectra from a sample. The system 200 includes a laser 202 that can be focused on the sample surface 204 supported on a substrate 206 to generate a laser-induced micro plasma. Optical emission from the plasma can be collected by a light collection component 210, such a fiber collimation lens oriented at 45° with respect to the laser beam, and focused onto an optical fiber 212. The other end of the fiber 212 can be coupled into a spectroscopic acquisition component 214, having a spectrometer and a detector. A processing component (e.g., a processor of a computing device) 216 receives the spectral data from the spectroscopic acquisition component 216.

Figure 3:
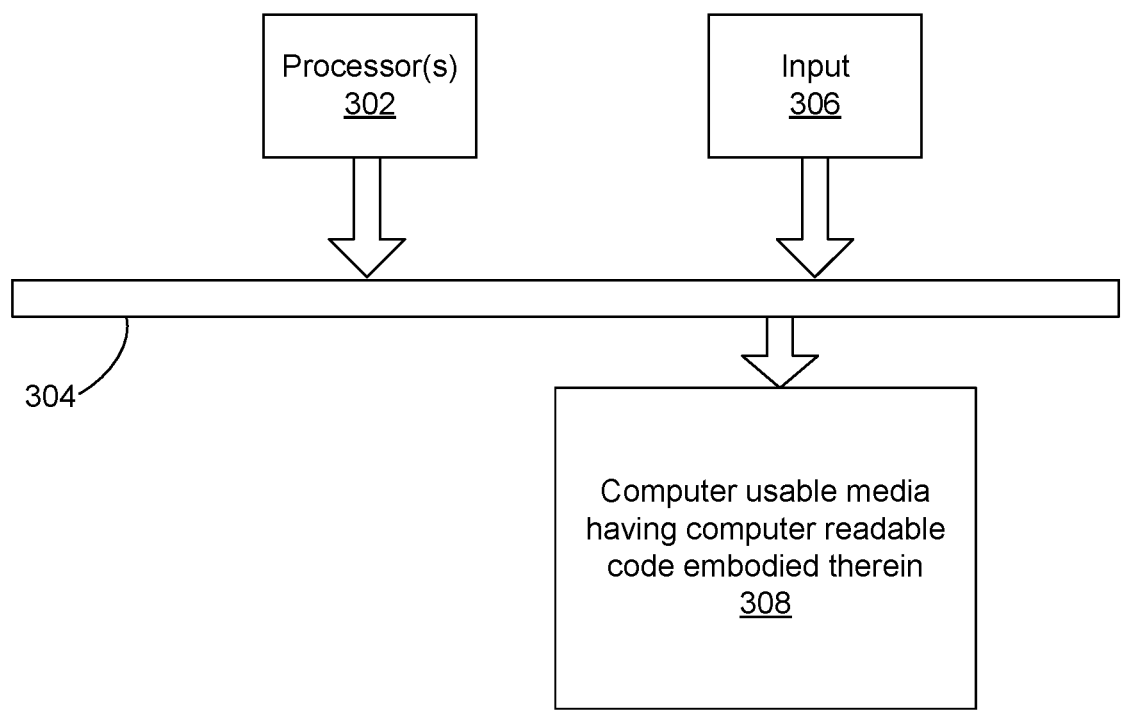
FIG. 3 is a diagram illustrating an example configuration of processors as used in implementing the improvements described herein.

In one embodiment, the processing component 216 can include a CPU, but other processors, such as ASICs or FPGAs are also within the scope of these teachings. Referring to FIG. 3, which is a schematic diagram of a system for training and using a machine learning model to diagnose a pathology, one or more processors 302 can be operatively connected by a connection component 304 (such as a computer bus) to an input component 306 and to non-transitory computer usable media 308. The one or more processors 302 are configured to train and/or use a machine learning algorithm diagnose the pathology or monitor progress of the pathology. The machine learning algorithm is trained on a training set that includes spectral data for LIBS collected optical emission from samples 204 of the predetermined biological fluid on the predetermined substrate 206, which have a known pathology or a known progress of the pathology by computer readable code embodied in the computer usable media 308.

In some implementations, the substrate 206 includes a Si wafer (unpolished side) onto which 5 µl drops of sample 204 are deposited and dried with a lamp. The samples 204 can be stored at −20° C., and, prior to deposition, thawed at 4° C. The substrate 206 can be loaded onto a motorized and computer-controlled x-y-z translation stage located within a chamber.

In some implementations, the laser 202 can include a Nd:YAG laser that emits 7 ns pulses of 1064 nm light, with an energy per pulse of 139 mJ (fluctuation less than 1%) and that focuses the light to a spot diameter 200 µm, with a repetition rate of 1 Hz.

In some implementations, the acquisition conditions include air at atmospheric pressure, a delay time of 1 µs, a gate width of 10 µs, and an intensified charge coupled device detector (ICCD) gain of 150.

In some implementations, the samples 204 can include blood plasma harvested from Alzheimer's Disease (AD) patients and Healthy Controls (HC) patients.

In some implementations, 5 µl drops of the plasma samples 204 can be pipetted on the substrate 206 and dried with an IR lamp (drying time~10 minutes; diameter of the deposited drops after drying~0.5 cm). After depositing a sample on the substrate 206, the substrate 206 can be mounted on the sample holder of the LIBS interaction chamber and ablated with light from the laser 202. The radiation emitted by the Laser-Induced Plasma (LIP) can be collected with the optical fiber 212, and coupled into the spectroscopic detection system 214, which can include a Mechelle Spectrograph and an ICCD. The plasma generation and the spectral acquisition can be synchronized with a delay/pulse generator.

To account for possible inhomogeneity in the liquid distribution of the samples on the substrate, multiple (e.g., 100) single shot spectra can be collected for each sample. To ensure that each spectrum came from a fresh spot on the surface of the dried plasma drop, the substrate can be displaced with respect to the incoming laser beam with a computer-programmable target holder. After each laser shot, the substrate can be displaced from the previous position. Single shot spectra can be acquired in each experiment, by displacing the sample through a computerized programmable translation stage under control by a motion controller 218 and ablating a fresh surface of the sample 204 with each laser shot. In this kind of experiment, the ablation process involves both the plasma sample and the underlying substrate, and therefore the emission spectra contain transitions from atoms coming from both the sample and the substrate.

In a first experiment, LIES spectra were collected for an exploratory data series and a full data series. The exploratory series included samples from 3 AD cases (samples labeled with VA codes: 22, 92, 100) and from 3 HC cases (samples labeled with VA codes: 96, 101, 103), and were collected with 9 single-shot spectra per sample (using a 3×3 spatial mapping pattern of the laser focus on the sample). The full data series included samples from 5 AD cases (samples labeled with VA codes: 99, 82, 100, 92, 22) and 5 HC cases (samples labeled with VA codes:104, 103, 101, 96, 93), and were collected with 125 single-shot spectra per sample (e.g., using five 5×5 mapping patterns of the laser focus on the sample). The experiment was carried out in double blind mode and the samples numbered from S1 to S10 as their UML-assigned sample identifiers. The correspondence between the VA codes and the UML-assigned sample identifiers is provided in Table 1, which shows the VA and UML numbering and classification of plasma samples used for the experimental series. Unlike all the other samples, #22 (S10) was contained in an unlabeled and uncapped test tube.

TABLE 1

| UML code | VA code | Classification |
|---|---|---|
| S1 | 99 | AD |
| S2 | 82 | AD |
| S3 | 104 | HC |
| S4 | 100 | AD |
| S5 | 92 | AD |
| S6 | 103 | HC |
| S7 | 101 | HC |
| S8 | 96 | HC |
| S9 | 93 | HC |
| S10 | 22 | AD |

Machine Learning Analysis
Data Preprocessing:

Prior to numerical analysis of the experimental data, two different data preprocessing procedures were carried out for the spectra of each sample: 1) all the spectra with total emission intensity lying outside of the interval (mean total emission intensity±standard deviation) were removed; 2) all the spectra with total emission intensity lying outside 10% of the mean total emission intensity were removed. This procedure allowed removing outliers due to two possible main sources of experimental fluctuations: laser energy fluctuation; and inhomogeneity of the plasma sample distribution on the Si substrate. The subsequent numerical analysis was performed with data pretreated in both ways, so to assess the most appropriate one based on the obtained classification accuracy. Since the number of outliers was not the same for each sample, the resulting number of selected spectra was also not the same, after the filtering procedure. Moreover, the spectral features of the main element of the substrate (Si), were removed from the spectra, so as to limit the possibility of the algorithms being trained based on with transitions that are not useful for classification of the samples and to avoid consequent mathematical artifacts. A further normalization aimed to scale the intensity of each spectral feature by referring them to a common range throughout the whole set of samples, with the following formula:

$$\frac{I_{i,S} - I_{i,min}}{I_{i,max} - I_{i,min}} \quad (1)$$

Here, the index i refers to the $i^{th}$ spectral feature, $I_{i,S}$, $I_{i,min}$ and and $I_{i,max}$ indicate respectively the emission intensity of the $i^{th}$ spectral feature in the given spectrum, S, in the spectrum where it has the minimum value, and in the spectrum where it has the maximum value.

The first rounds of classification experiments were carried out using only the mentioned preprocessing. An analysis of the average emission intensity of each sample, though, showed some variability between the average emission intensity of the various samples, likely due to experimental factors (e.g., laser energy drift; tilt of the sample holder), and additional series of classifications were also carried out by using additional data pretreatment, i.e., by normalizing each spectrum of a given sample to the mean intensity of the spectrum itself.

Algorithms:
Machine Learning Approach

The second part of the classification experiment established that machine learning tools applied to LIBS spectra can discriminate between healthy and diseased samples despite the fact that the direct analysis does not yield conclusive indications. Five algorithms were considered, with the intent to compare their performance and identify the most suitable for the present task: Linear Discriminant Analysis (LDA), Fisher Discriminant Analysis (FDA), Support Vector Machines (SVM), Random Forest and Boosting Algorithms, such as Gradient Boosting.

Linear Discriminant Analysis (LDA) is a supervised learning approach that identifies the separating hyperplanes between different classes by assuming normal class-conditional distribution models (see, for example, Alaa Tharwat et al., Linear discriminant analysis: A detailed tutorial, AI Communications 00, IOS Press, 2017, which is incorporated by reference herein in its entirety and for all purposes). Features are projected to linear vector subspaces and then classified. The class of an unknown sample was determined by computing score values for the various classes using the score functions and data features, and the sample was assigned using maximum likelihood decision rules. Feature extraction was done using the statistical dependency (SD) between features and associated class labels with a quantized feature space (see, J. Pohjalainen, O. Rasanen, S. Kadioglu, Comput. Speech Lang. 29 (2013) 1, which is incorporated by reference herein in its entirety and for all purposes), in order to limit the contribution of non-discriminatory data points, reduce the dimensionality of the original dataset and avoid over fitting. FDA is a similar learning approach to LDA and is used for discrimination between two classes (see, for example, Max Welling, Fisher Linear Discriminant Analysis, which is incorporated by reference herein in its entirety and for all purposes). Support vector machines (SVM) is a discriminative classifier that distinguishes one class from another by finding an optimal hyperplane that maximizes the separation between the two classes (see, for example, Nikolay Stanevski, Dimiter Tsvetkov, Using Support Vector Machine as a Binary Classifier, International Conference on Computer Systems and Technologies—CompSysTech' 2005, which is incorporated by reference herein in its entirety and for all purposes). The members of both classes that are closest to the hyperplane serve as support vectors. The separating hyperplane is selected by optimizing the margin between the two classes. For data whose feature space is nonlinear, a kernel is used to transform the data into a linear space (T. Hastie, R. Tibshirani, J. Friedman, The Elements of Statistical Learning: Data Mining, Inference, and Prediction, Springer, New York, 2009, L. Liang, T. Zhang, K. Wang, H. Tang, X. Yang, X. Zhu, Y. Duan, H. Li, Appl. Opt. 53 (2014) 544, which are incorporated by reference herein in their entirety and for all purposes). In this work the support vector machine implementation within the Waikato Environment for Knowledge Analysis (WEKA) software with a second-degree polynomial kernel was used. A ten-fold cross validation was performed.

For LDA, FDA and SVM, the average spectrum of the clean PVDF substrate was subtracted from the spectra of the fluids deposited on the substrate itself. In both cases, each spectrum with total integrated area that did not fall within one standard deviation about the average for the 100 shots were rejected, while the remaining were normalized by their total integrated area. All calculations were performed using MATLAB. The analysis was performed over the spectral range 250-680 nm to limit the computational cost while at the same time including the spectral region with the most meaningful spectral transitions.

Random forests, or random decision forests, is an ensemble learning method for classification, regression, and other tasks that operates by constructing a multitude of decision trees at training time and outputting the class that is the mode of the classes (classification) or mean prediction (regression) of the individual trees. (See Tin Kam (1995). Random Decision Forests, Proceedings of the 3rd International Conference on Document Analysis and Recognition, Montreal, QC, 14-16 Aug. 1995. pp. 278-282, which is incorporated herein by reference.) Random decision forests can correct for decision trees' habit of overfitting to their training set.

Boosting is a machine learning meta-algorithm that combines a set of weak classifiers into a strong classifier. A weak classifier usually has a simple structure and may perform only slightly better than random guessing. These weak classifiers are typically trained iteratively and ensembled in a special way (e.g., weighted according to their individual accuracy) to boost the overall performance of the classifier. We used the regression tree as the weak classifier in our experiments. The Gradient Boosting algorithm considers additive models of the following form:

$$F(x) = \sum_{m=1}^{M} \alpha_m h_m(x) \quad (2)$$

where $F(x)$ is the final model, $h_m(x)$ are the weak classifiers, and am are the weights for each weak classifier determined by its performance. The additive model is built in a forward stage-wise fashion:

$$F_m(x) = F_{m-1} + \alpha_m h_m \quad (3)$$

At each stage, the model tries to choose a model that satisfies the following equation:

$$y = F_i(x) + h_i \quad (4)$$

where y indicates the true classification of sample x, and $y - F_i(x)$ are called residuals. These are the parts that existing model is not able to calculate appropriately. To compensate for these residuals during each stage, the gradient boost model employs an iterative process for the construction of the additive model. At each iteration, the model attempts to choose a weak classifier that compensates the residuals of the existing model. Ultimately, this process minimizes the overall cost function.

AdaBoost, short for Adaptive Boosting, is a machine learning meta-algorithm that can be used in conjunction with many other types of learning algorithms to improve performance. The output of the other learning algorithms ('weak learners') is combined into a weighted sum that represents the final output of the boosted classifier. AdaBoost is adaptive in the sense that subsequent weak learners are tweaked in favor of those instances misclassified by previous classifiers.

In the first round of classifications, four machine learning algorithms were tested: Support Vector Machines (SVM); Random Forest; Adaboost; Gradient Boost. All of them are supervised algorithms, i.e., they have to be trained with data with a library of labeled data.

After the training of the algorithms, the algorithms were applied to classify unknown data of the same kind. In this study, all the spectra were labeled (either as AD or as HC), and thus there was no actual unknown data. Therefore, the learning and classifications phases were carried out by dividing the group of spectra in two subsets and using a cross-validation approach, i.e., one subset was used to train the algorithms, and the other to test it. Two different leave-one-out cross validation (LOOCV) methods were used to build the subsets and test the algorithms. In the first, all spectra from all samples were collectively used to train the algorithm, and only one spectrum (or a small subset of spectra) was left out for testing it. In the second, spectra from all samples but one were used for the learning phase, and then the algorithm was tested on the spectra of the one sample that was left out. At the end of the whole process, in both approaches, every spectrum and every sample is used both for learning and for testing (though obviously not at the same time). The first approach tends to overestimate the classification accuracy but is the only possibility when only few samples are available. The second approach provides a more realistic estimation of the performance of the algorithm but requires a large set of samples to meaningfully train the algorithm. In the following, the first approach will be referred to as "leave one spectrum out", and the second as "leave one patient out". The first method can be also performed choosing a slightly larger subset of data for cross-validation, which provides a slightly lower accuracy than the LOOCV, but speeds up the classification and reduces the computational cost. A 5-fold classification accuracy was used for some classification runs (i.e., all spectra but 5 are the training subset, and the remaining 5 spectra are the test subset).

In all cases, the metrics used to evaluate the performance of the algorithms were the following:

Positive Predictive Value (PPV) or sensitivity, the percentage of spectra correctly classified as diseased or percentage of true positives;

Negative Predictive Value (NPV) or specificity, the percentage of spectra correctly classified as healthy or percentage of true negatives; and Total Classification Accuracy, the percentage of spectra correctly classified as either healthy or diseased.

An important by-product of classification algorithms is a ranked list of top features, i.e., the wavelengths that contribute the most to classification. This can provide information about the possible presence of elements responsible for the differences between healthy and diseased samples, and thus help identifying trends. The ranked list of top features were compared with spectra and assigned to specific transitions and elements with the help of atomic spectra databases (e.g., from NIST and Kurucz).

Results:

In the first series of calculations, the performance of four algorithms were compared with a 5-fold cross validation approach and using the first 200 top features for classification. Results of these calculations are reported in Table 2 and show that the Gradient Boost algorithm performed best. In particular, Table 2 shows a comparison between different classification algorithms and number of employed top features with spectra filtered by removing the spectra with total emission intensity lying outside 10% of the mean total emission intensity (identified as 10% in the table) and by removing the spectra with total emission intensity outside one standard deviation around the mean (identified as SD in the table), with 5-fold cross validation.

To test if a further improvement of the classification performance could be obtained by increasing the number of included top features, Gradient Boost was also tested with 500 features. This provided only a very moderate improvement of the classification performance, and in the following calculations 200 features were considered the optimal value.

TABLE 2

| | Classification Accuracy | Sensitivity | Specificity |
|---|---|---|---|
| 10%, 5-fold cross validation, Top 200 features | | | |
| SVM | 80.75% | 74.52% | 87.20% |
| RF | 84.48% | 81.47% | 87.60% |
| Adaboost | 88.41% | 88.80% | 88.00% |
| Gradient Boost | 90.96% | 91.51% | 90.40% |
| 10%, 5-fold cross validation, Top 500 features | | | |
| Gradient Boost | 91.16% | 91.51% | 90.80% |
| SD, 5-fold cross validation, Top 200 features | | | |
| SVM | 81.51% | 71.37% | 92.15% |
| Random Forest | 85.45% | 80.34% | 90.81% |
| Adaboost | 88.73% | 88.03% | 89.46% |
| Gradient Boost | 92.45% | 92.31% | 92.60% |
| SD, 5-fold cross validation, Top 500 features | | | |
| Gradient Boost | 91.47% | 90.17% | 92.83% |

As previously mentioned, the "leave-one-patient-out" approach can provide a meaningful cross validation method. The results of the leave-one-patient-out method, which were obtained with the Gradient Boosting algorithm, are reported in FIGS. 4A and 4B.

Figure 4A:
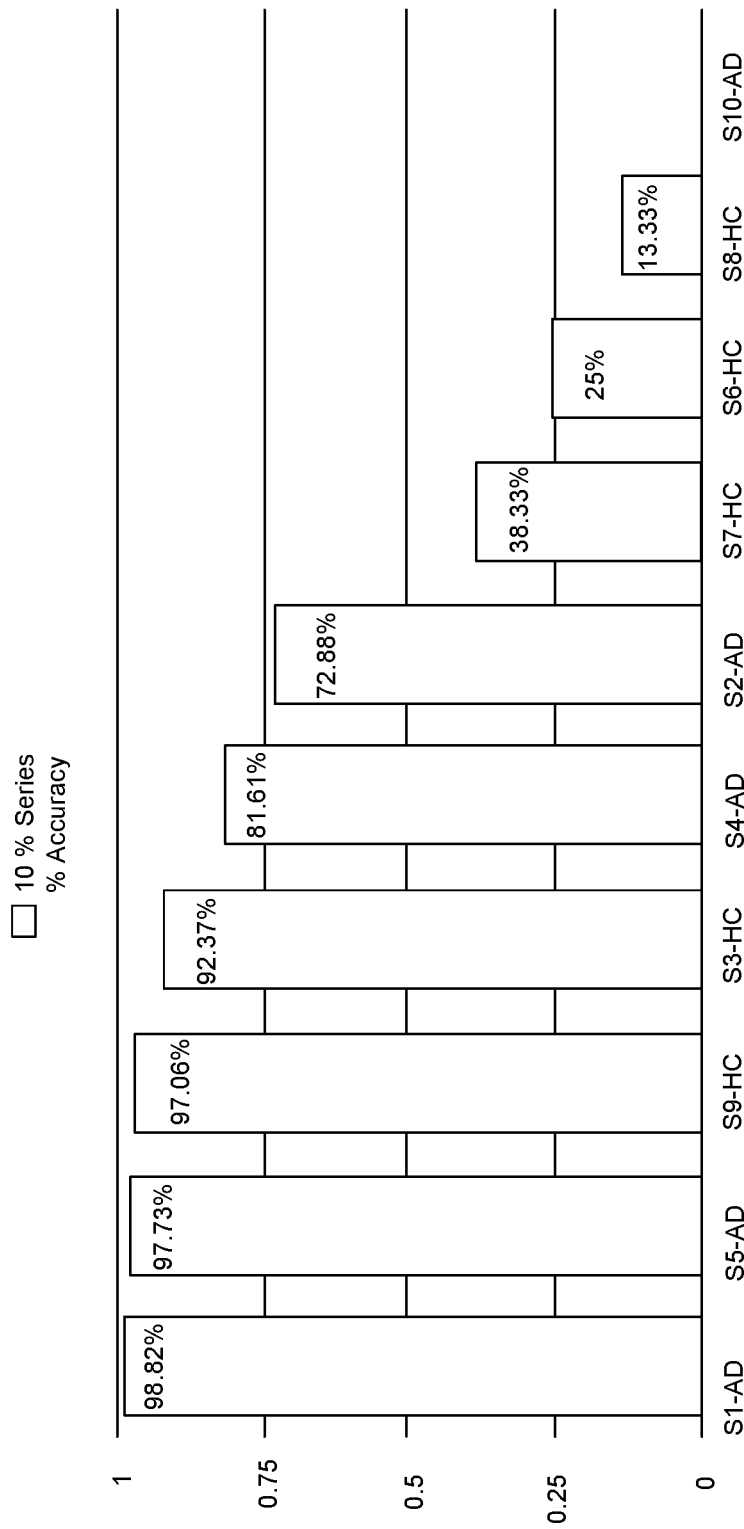
FIGS. 4A and 4B are bar graphs showing the percentage of accurate predictions of different samples using the machine learning classifier that is trained on spectra of labelled samples other than the one whose class is predicted.
Figure 4B:
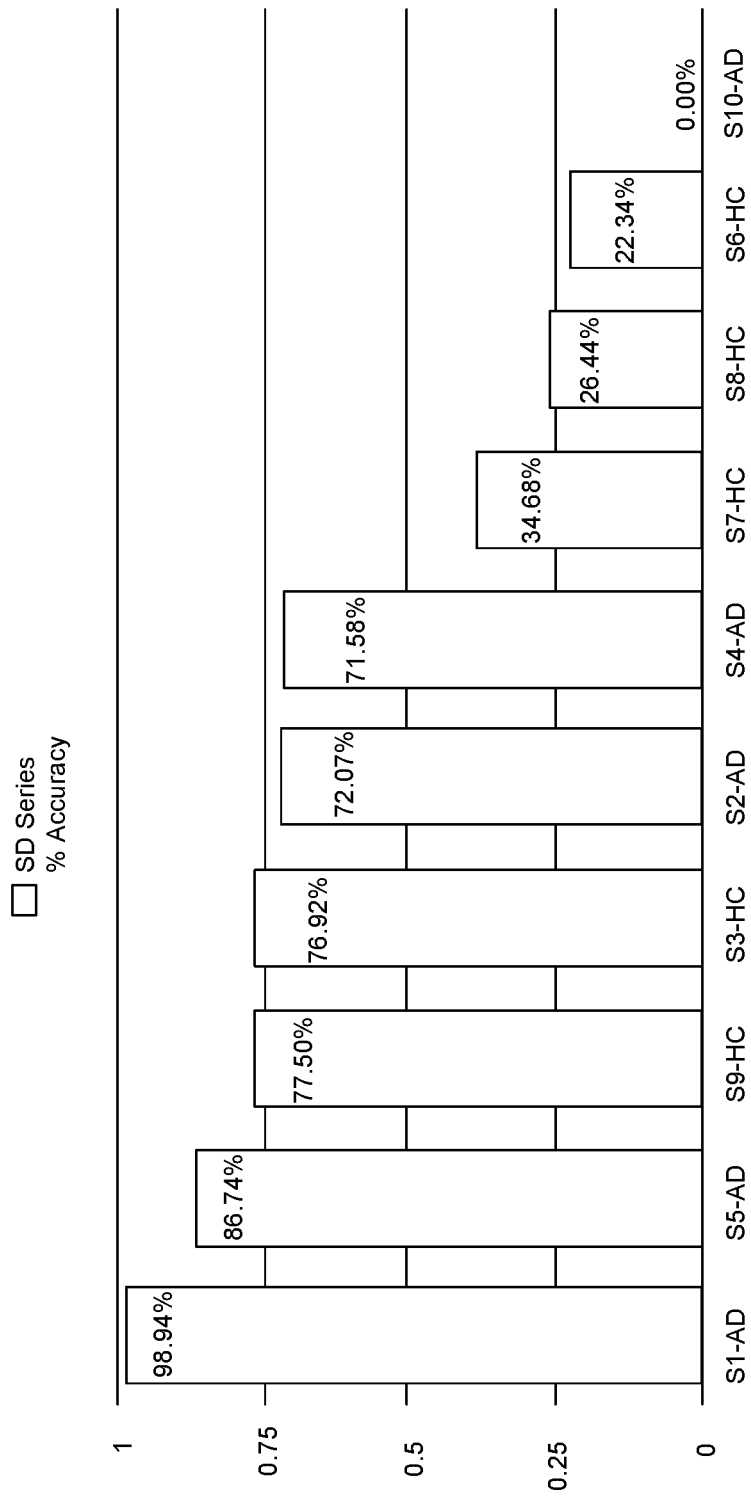

FIGS. 4A and 4B are bar graphs showing the percentage of accurate predictions of different samples using the machine learning classifier that is trained on labelled samples other than the one whose class is predicted. FIGS. 4A and 4B show that 4 samples (3 HC: S6, S7, S8, and 1 AD: S10) were not correctly classified (i.e., had a classification accuracy of less than 50%), while the others are correctly classified with high accuracy, in particular, in the calculation run with spectra with total emission intensity lying within 10% around the mean total emission intensity shown in FIG. 4A. Although encouraging, these results may not be considered conclusive, for two main reasons: 1) the number of samples is relatively low for the leave-one-patient-out cross validation method; and 2) the presence of a classification accuracy value equal to zero (for S10) can indicate the occurrence of experimental or numerical artifacts. To rule out the possibility of artifacts, two more rounds of calculations were run. In the first, the sample S10 was removed from the set: this possibility was suggested by the fact that S10 (i.e., sample 22 in the VA numbering) was stored in an uncapped and unlabeled test tube, which could have led to incorrect labeling. The results are reported in FIGS. 5A and 5B, which show that without sample S10 only one sample is not correctly classified (S8, HC), and that the overall classification accuracy increases considerably when the misleading sample is removed.

The second additional series of calculations was performed with a different approach that included an additional normalization step added to account for the average intensity not being identical for each sample. To account for this variability and to avoid the spectra with higher average emission intensity to drive the calculation, each spectrum was normalized by dividing it for its own average emission intensity. The calculation with Gradient Boosting was then run both with all 10 samples and without S10. The results are presented in FIGS. 6A and 6B and FIGS. 7A and 7B, respectively.

Table 3 shows comparison between the average total classification accuracy of the gradient boosting for the four main rounds of leave-one-patient-out cross validation. Based on the results presented in FIGS. 4A, 4B, 5A, 5B, 6A, 6B, 7A, 7B, and summarized in Table 3, some trends are observable, and some conclusions may be drawn. For example, removing sample S10 (i.e., sample 22) from the training of the machining learning algorithm had a beneficial effect on the classification accuracy, and is justified by the different storing conditions and by the absence of a clear label. Therefore, this sample will not be used in the next series of laboratory and computational experiments. Also, when using both the normalization over the mean emission intensity and the scaler normalization shown in eq.1, higher classification accuracy is obtained when using spectra with total emission intensity filtered with the SD deviation filter than with the 10% filter. The opposite is true when the normalization over the mean emission intensity is not used. This behavior can be rationalized based on the fact that with the SD filter, more spectra are available for training the algorithm and for classification, which represents an intrinsic advantage. On the other hand, when the spectra are not normalized, this advantage is not exploited, because the relatively higher variability of the emission intensity (that, with the SD filter is around 20%) is not accounted for, and better results are obtained with the 10% filter and a consequently lower variability of the emission intensity. Furthermore, despite the total classification accuracy obtained by normalizing the spectra over the average emission intensity being lower than the accuracy obtained by skipping this step (when S10 is removed), it may be advisable to proceed with this normalization to scale the emission intensity of all samples and rule out the possibility of creating numerical artifacts in the classification. Also, increasing the number of samples can be helpful to further improve the classification accuracy and will allow carrying out blind and double-blind tests.

TABLE 3

Average Total Classification Accuracy

Figure 5A:
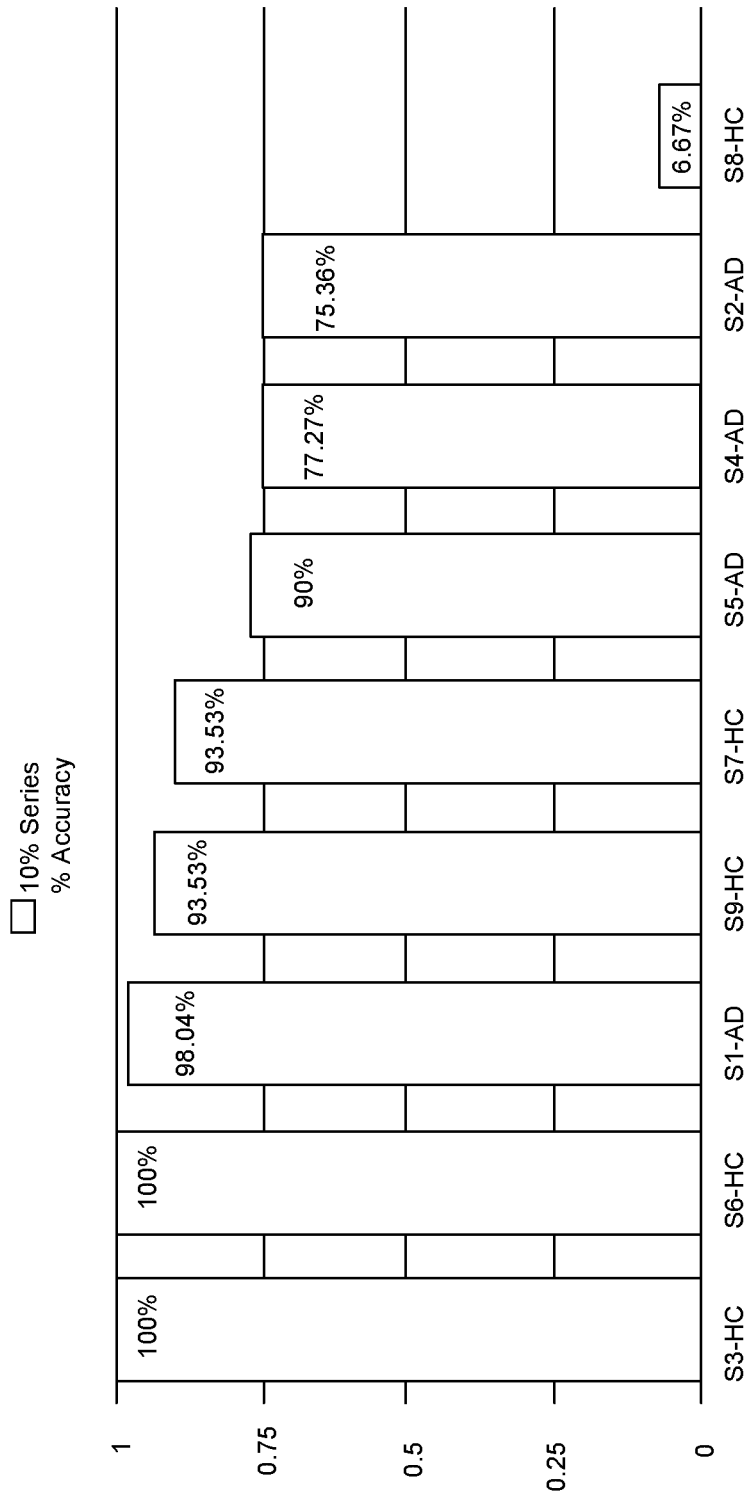
FIGS. 5A and 5B are bar graphs showing the percentage of accurate predictions of different samples using the machine learning classifier that is trained on spectra of labelled samples other than the one whose class is predicted when a spurious sample is removed from consideration.
Figure 5B:
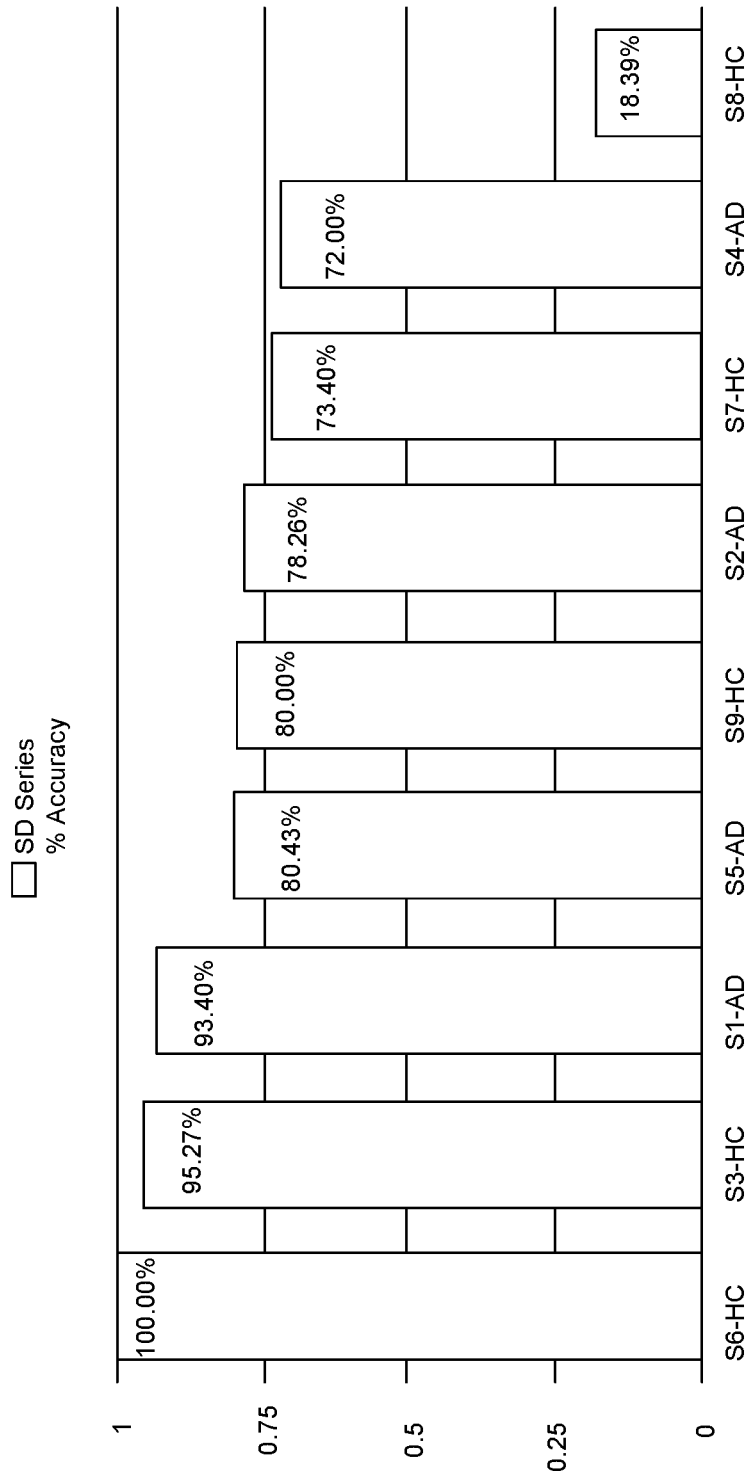
Figure 6A:
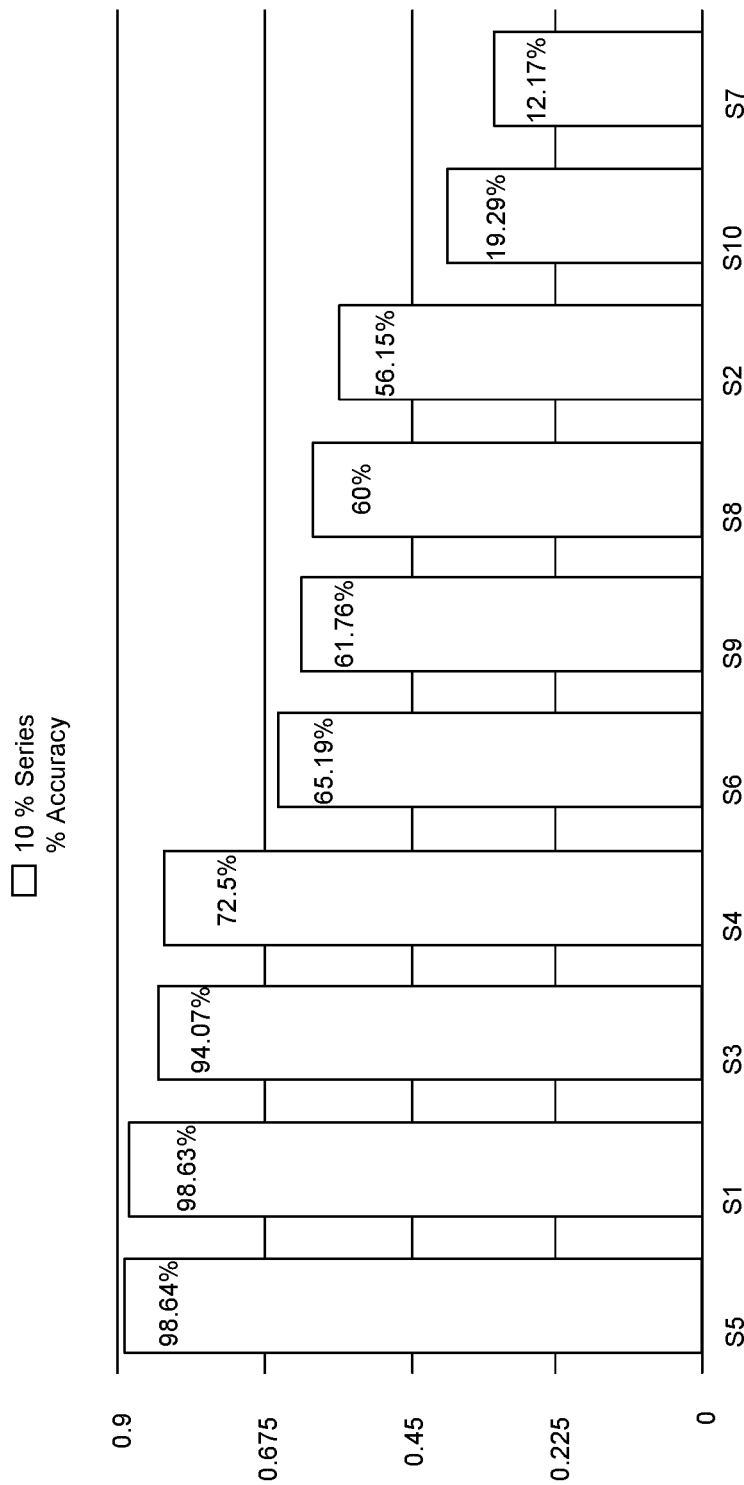
FIGS. 6A and 6B are bar graphs showing the percentage of accurate predictions of different samples using the machine learning classifier that is trained on intensity-normalized spectra of labelled samples other than the one whose class is predicted.
Figure 6B:
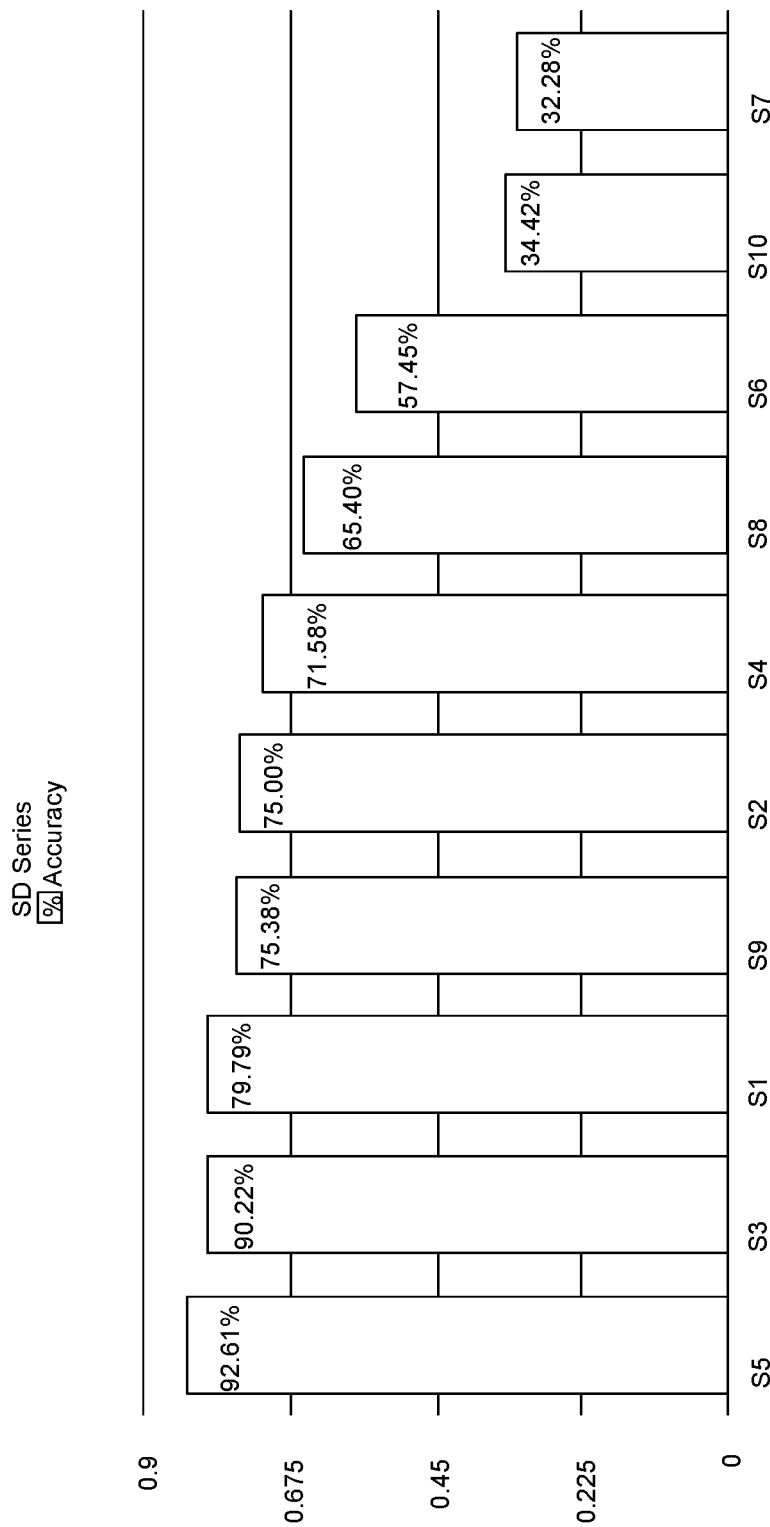
Figure 7A:
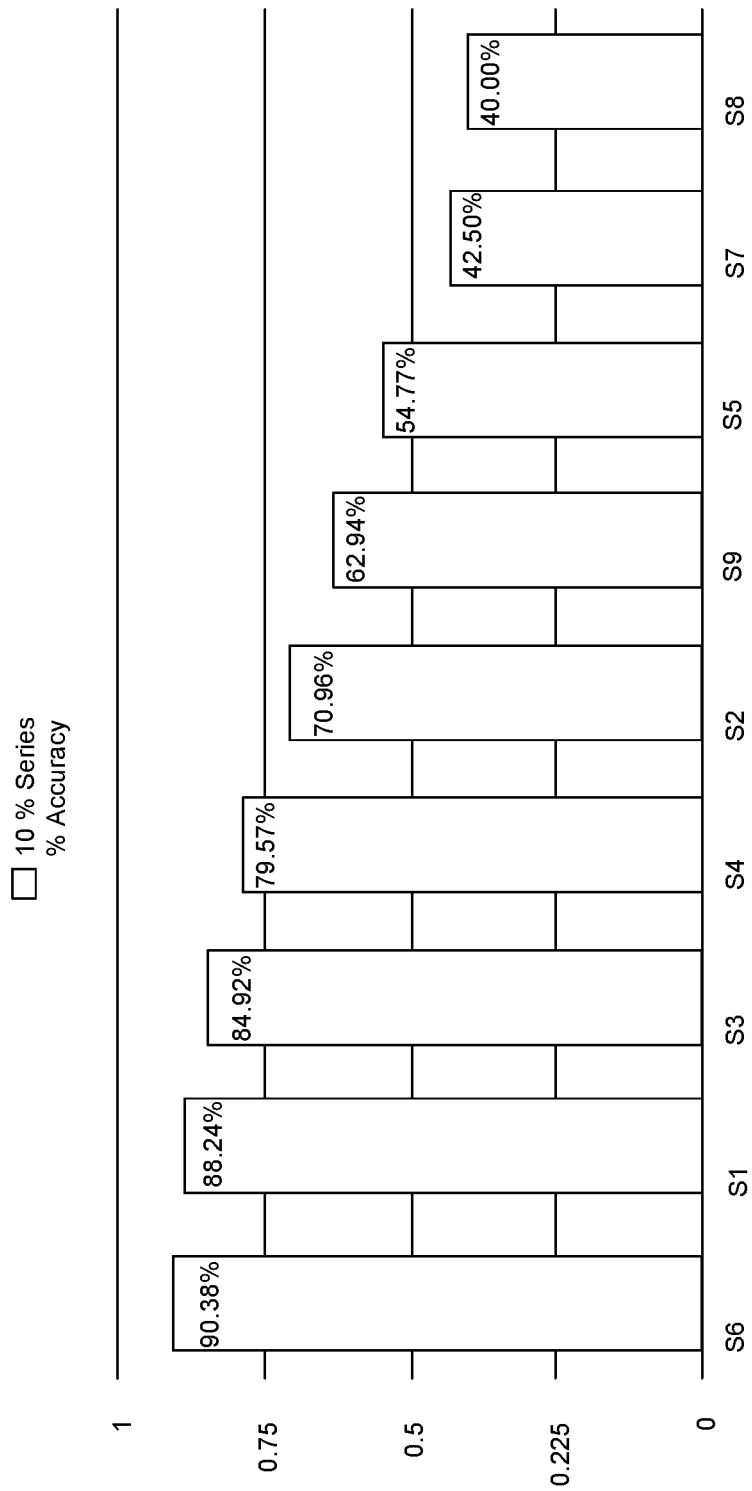
FIGS. 7A and 7B are bar graphs showing the percentage of accurate predictions of different samples using the machine learning classifier that is trained on intensity-normalized spectra of labelled samples other than the one whose class is predicted when a spurious sample is removed from consideration.
Figure 7B:
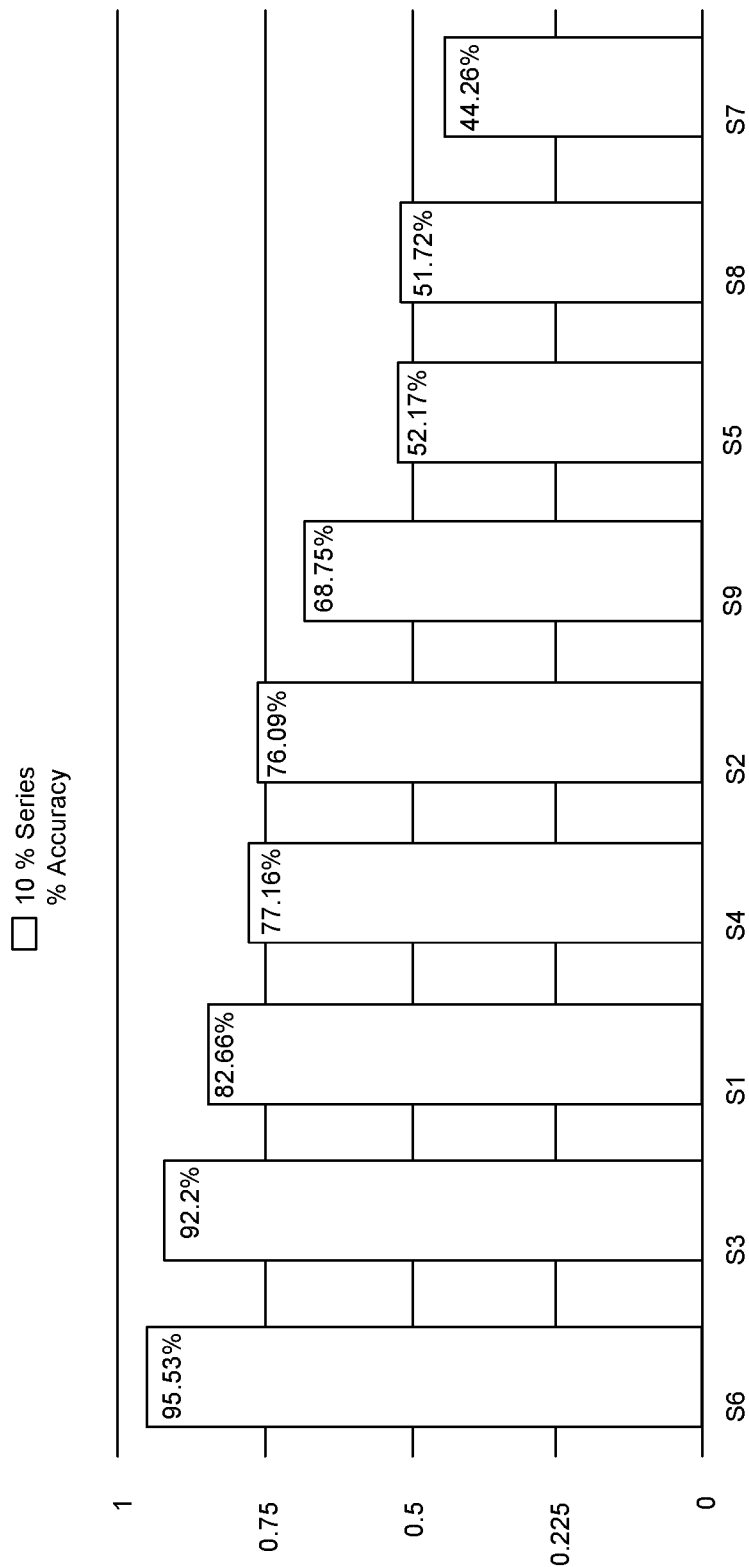

| | | 10% series | SD series |
|---|---|---|---|
| FIGS. 4A, 4B | All samples, no mean normalization, scaler normalization | 61.71% | 56.72% |
| FIGS. 5A, 5B | No S10, no mean normalization, scaler normalization | 79.56% | 76.79% |
| FIGS. 6A, 6B | All samples, both mean and scaler normalization | 64.84% | 65.48% |
| FIGS. 7A, 7B | No S10, both mean and scaler normalization | 68.14% | 71.17% |

Top Spectral Features

As previously mentioned, a useful byproduct of the classification process are the ranked lists of spectral features that contribute the most to the classification accuracy. The calculations in this report were run with a maximum of 200 top spectral features, beyond which the classification accuracy did not further improve. Analysis of the ranked lists of top spectral features is important for two main reasons: 1) to investigate which transitions and which species are responsible for the differentiation of healthy and diseased samples and to gain insight into the possible role of different elements in the onset and progress of the disease; and 2) to rule out the possibility of numerical artifacts. For these reasons, the 50 top features for each of the described calculation runs were assigned and compared with each other. The first aspect that we checked was if the top features were actual spectral features. Table 4 reports the percentage of top features that do not correspond to actual features in each of the calculations, indicated as "non-peaks" in the table. In particular, Table 4 shows percentage of non-peaks in the top 50 features contributing to the classification with the gradient boost algorithm for the four main rounds of leave-one-patient-out cross validation.

These percentages indirectly confirm the conclusions of the previous paragraph, i.e., a higher number of non-peaks (and thus, of potential numerical artifacts) is found for the 10% series and when no mean normalization is performed. The reason for this behavior can be ascribed to the fact that with fewer spectra to train from (10% series) the algorithm can incur overfitting issues and use non-significant variables (such as the background signal) for classification. This confirms the previously reached conclusions that the SD series is more trustworthy and that normalizing each spectrum over the mean emission intensity is the best practice.

TABLE 4

Percentage of non-peaks

| | | 10% series | SD series |
|---|---|---|---|
| FIGS. 4A, 4B | All samples, no mean normalization, scaler normalization | 42% | 18% |
| FIGS. 5A, 5B | No S10, no mean normalization, scaler normalization | 34% | 20% |
| FIGS. 6A, 6B | All samples, both mean and scaler normalization | 40% | 12% |
| FIGS. 7A, 7B | No S10, both mean and scaler normalization | 32% | 13.7% |

Even more importantly, the top features corresponding to actual peaks do not appear to be significantly affected by the different preprocessing methods, that is, the same peaks and the same species are identified as the most discriminating in virtually all the calculation runs. This shows that, despite the overfitting issues, even with the 10% series no actual artifact was generated, and the resulting features have a physical meaning and may be used to deduce biological information from the LIBS spectra.

Some of the recurring transitions are reported in Table 5, which shows the wavelengths of some of the most discriminating spectral features. For the transitions that were listed in databases, the corresponding emitting species are indicated. For the other, a question mark is reported instead. Transitions for which the emitting species is reported with a question mark indicate that the assignation has a high degree of uncertainty. Table 5 shows that transitions from some elements (Mg, Fe, Al, Na, Ca) contribute to the discrimination between healthy and diseased samples. The identification of these transitions, though, is limited by the available databases, that do not list several of them (indicated with a question mark in the table).

TABLE 5

| Wavelength (nm) | Species |
|---|---|
| 279.55 | Mg II |
| 280.40 | Mg II |
| 284.02 | ? |
| 302.06 | Fe I |
| 309.28 | Al I |
| 324.82 | ? |
| 380.89 | ? |
| 388.29 | Fe I (?) |
| 396.15 | Al I |
| 398.36 | V I (?) |
| 401.35 | Fe I (?) |
| 404.87 | ? |
| 431.86 | Ca I |
| 556.42 | N I (?) |
| 572.25 | ? |
| 572.68 | ? |
| 589.00 | Na I |
| 589.59 | Na I |
| 607.01 | ? |
| 615.42 | Na I |
| 616.21 | Ca I |
| 678.35 | ? |

Although the above-described approached proved that machine learning techniques can be used to classify spectra as being from an AD sample or from a HC control sample, the limited number of samples used in the experiments meant that the classification accuracy results depended on the particular samples used in the experiments. It was evident that improved techniques were needed to handle larger sample sets.

The success of a machine learning algorithm can depend on the training data set used and the features of the training data considered. When two objects (e.g., spectra) have similar features, it can be difficult to identify features that distinguish them from features that characterize the objects but that may not distinguish them.

Figure 8A:
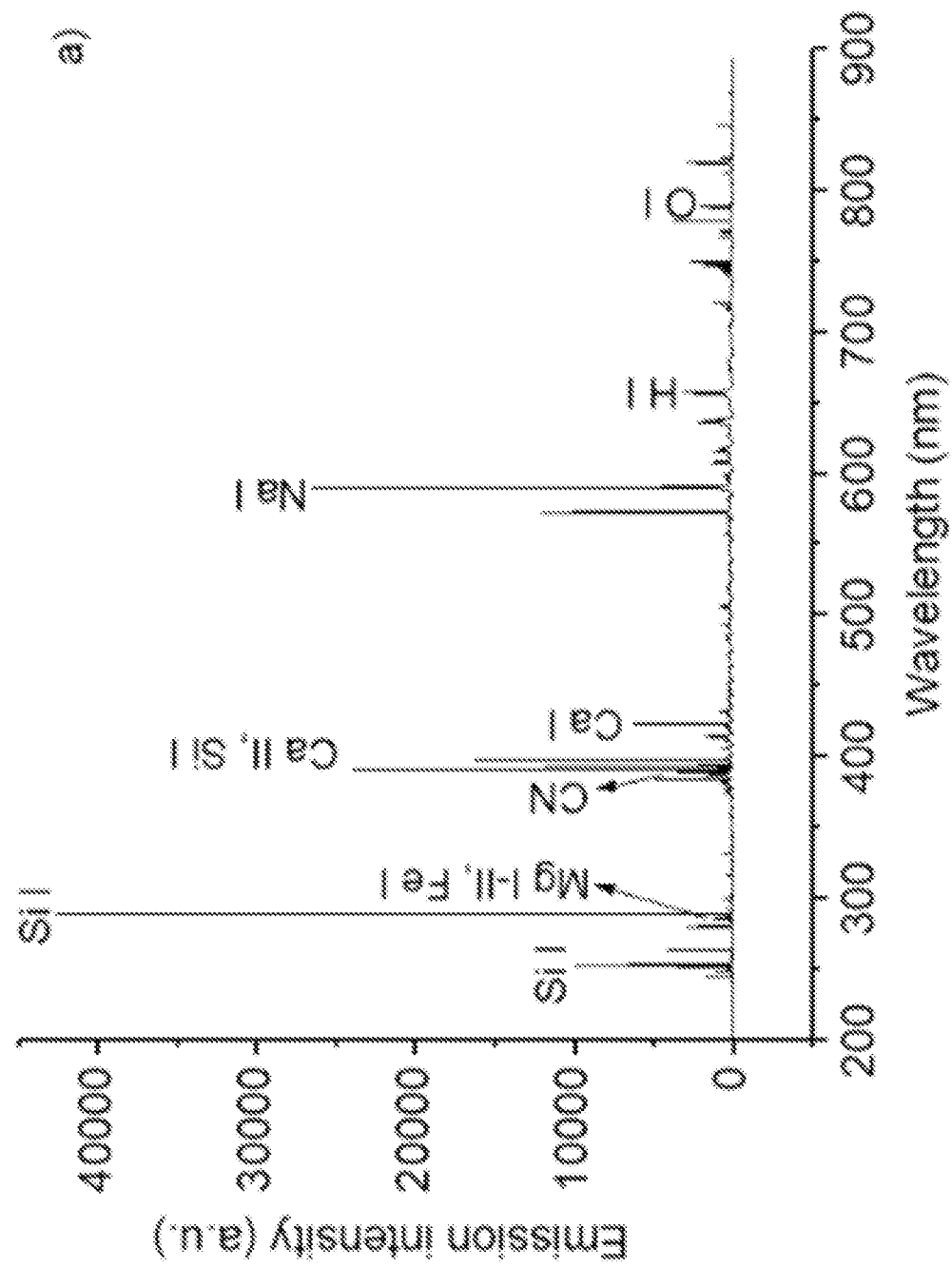
FIG. 8A is an example LIBS spectrum of plasma from an AD patient.
Figure 8B:
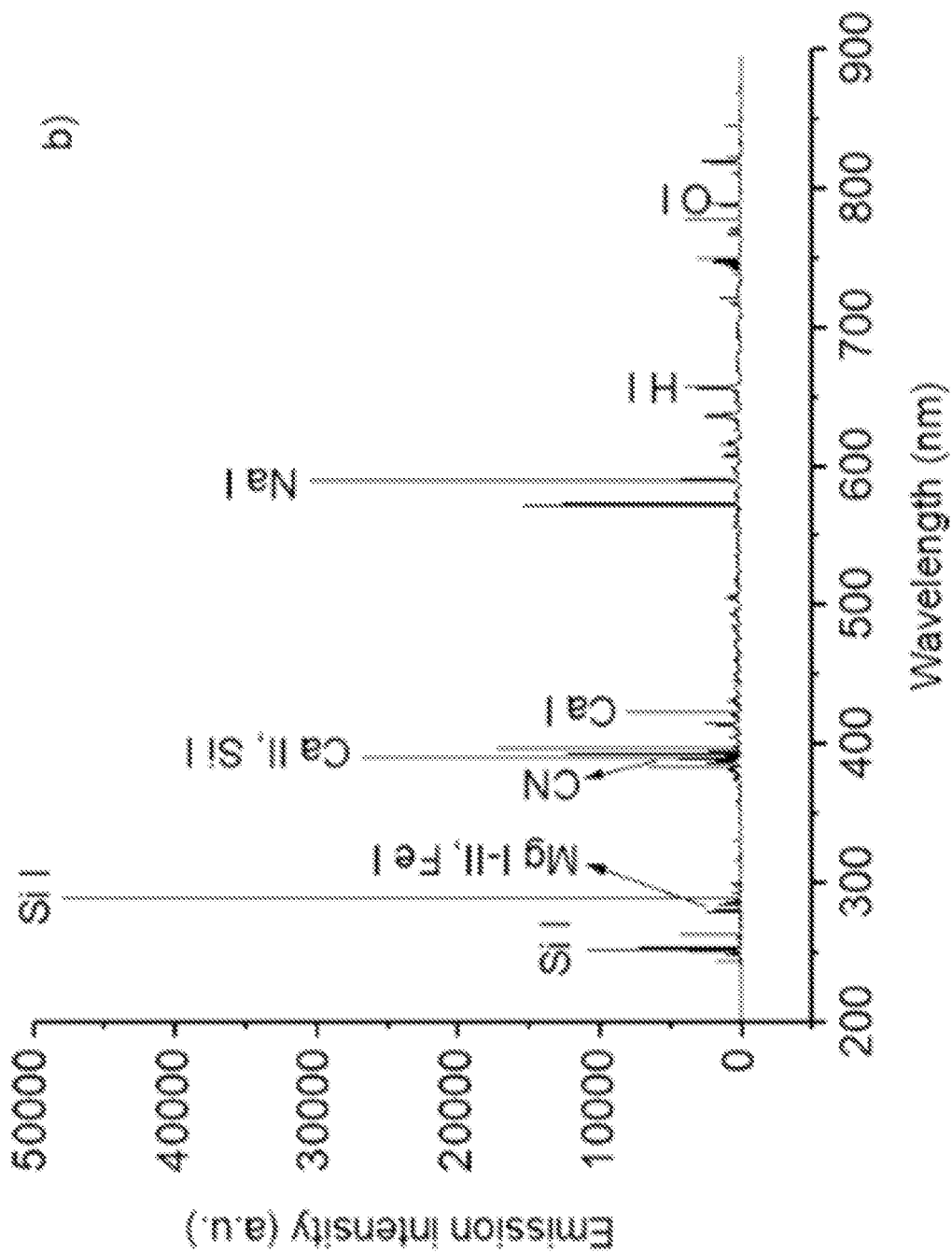
FIG. 8B is an example LIBS spectrum of plasma from a HC subject.

To identify salient features of the spectra to use to train a machine learning algorithm to classify a spectrum as a being from a healthy or diseased patient, a difference spectrum technique can be used. FIG. 8A shows an example of LIBS spectrum of plasma from an AD patient and FIG. 8B shown an example LIBS spectrum of plasma from a HC subject. These figures shows that there is no clearly distinguishable difference between the two classes, as the spectra are virtually identical, and therefore LIBS spectra as such do not appear to provide an obvious discrimination between AD and HC samples. The species responsible for the emission of some of the main peaks are identified in the two spectra.

Figure 9:
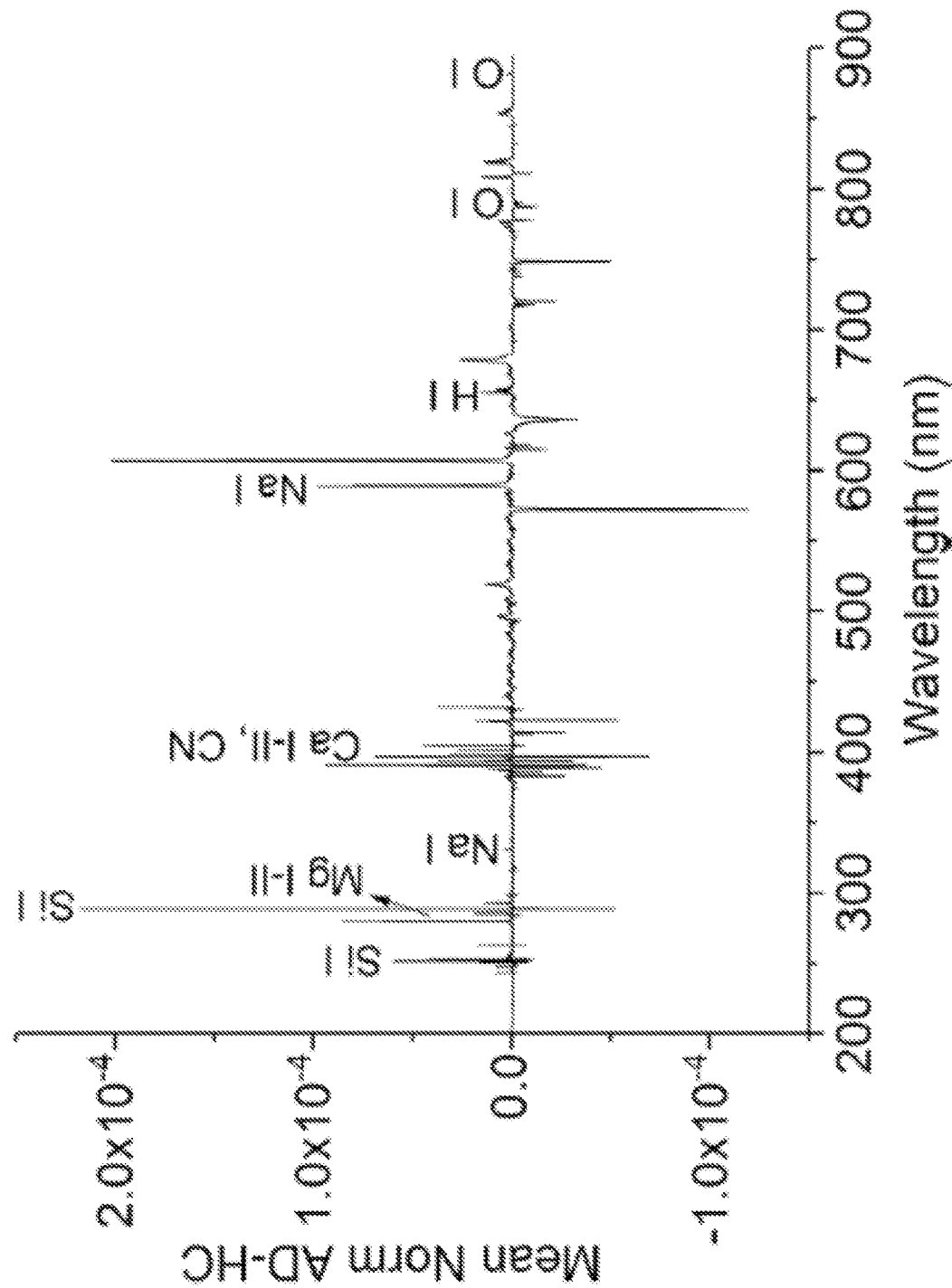
FIG. 9 is a difference spectrum that displays positive and negative peaks that characterizes the difference between a mean AD LIBS spectrum and a mean HC LIBS spectrum.

To differentiate the AD and HC classes of samples, we generated difference spectra as a preprocessing step to enhance spectral differences between AD and HC samples, so as to identify salient features of the spectra to use for training the machine learning algorithms and for using the machine learning algorithms to classify samples. In another experiment, a group of 23 samples (11 AD and 12 HC) was selected randomly from a pool of AD and HC subjects as our training set and used to obtain mean AD and mean HC spectra. After normalizing each spectrum over its total emission intensity, we subtracted the mean HC spectrum from the mean AD spectrum. FIG. 9 is a difference spectrum that displays positive and negative peaks that characterized the difference between the mean AD spectrum and the mean HC spectrum and is representative of the differences between AD and HC samples.

The transitions appearing as positive or negative peaks in FIG. 9 indicate an enrichment (positive) or a depletion (negative) of the given emitter in AD samples with respect to HC ones. Therefore, the difference spectrum was used as a model template to diagnose 66 testing spectra that corresponded to 44 different patients. Samples from 10 of these patients were acquired more than once, and their spectra were treated independently as belonging to different patients. For each unknown sample, we computed a difference spectrum, using a similar procedure to that described above.

A mean HC spectrum was determined and subtracted from each of the unknown spectra. This provided a difference spectrum for each unknown, that we compared with the model. Since the latter was obtained as the AD spectrum minus the HC spectrum, it was assumed that if transitions in the unknown difference spectra had the same polarity as in the model, they should be classified as AD, and if the opposite polarity, as HC.

Figure 10A:
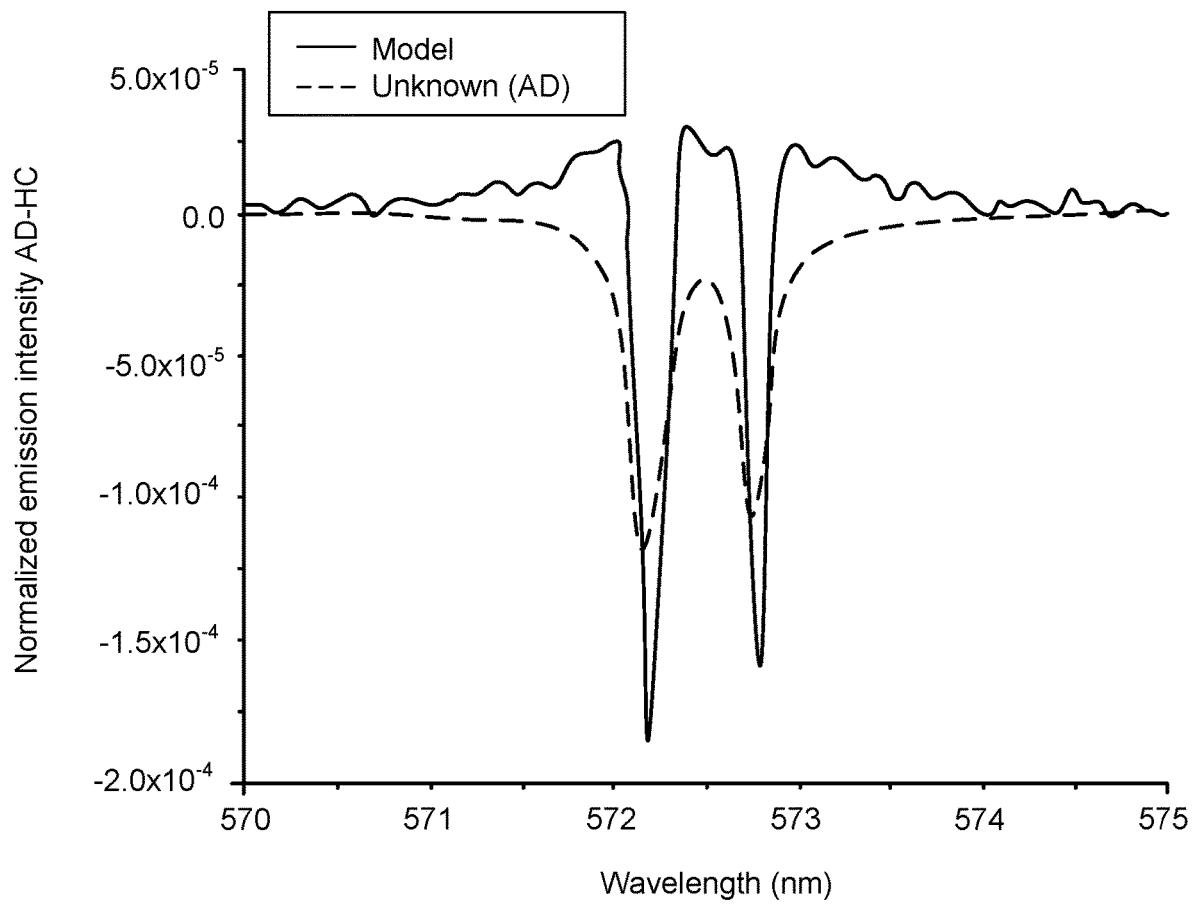
FIG. 10A is a portion of a spectrum for a first unknown sample in the spectral region 570-575 nm compared to a model spectrum.
Figure 10B:
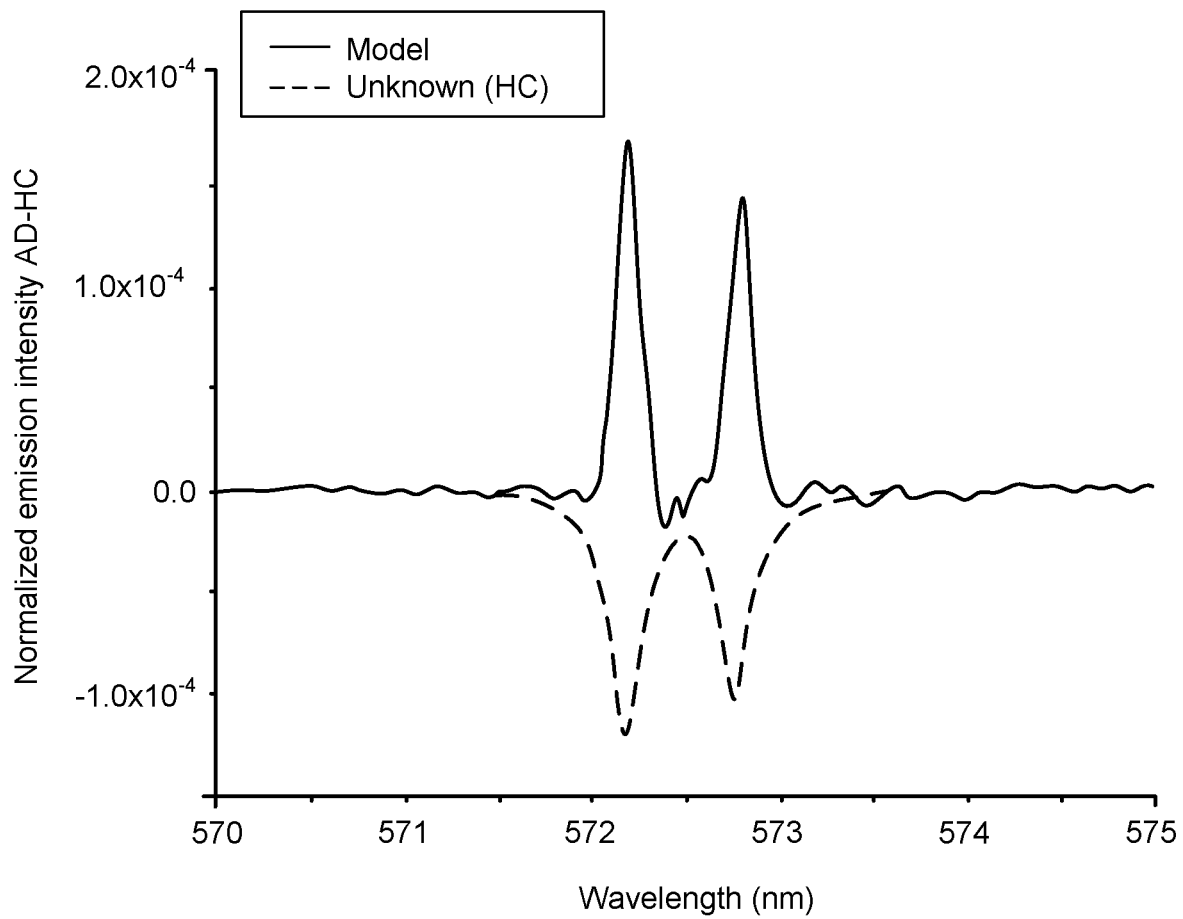
FIG. 10B is a portion of a spectrum for a second unknown sample in the spectral region 570-575 nm compared to the model.

FIG. 10A is a portion of a spectrum for a first unknown sample (dashed line) in the spectral region 570-575 nm compared to the model, and FIG. 10B is a portion of a spectrum for a second unknown sample (dashed line) in the spectral region 570-575 nm compared to the model. FIGS. 10A and 10B shows an unambiguous difference between the spectrum from the first sample, which is determined be from an AD patient, because it has the same polarity as in the reference model, and the spectrum from the second sample, which is determined to be from a HC patient, because it has the opposite polarity to that of the reference model. This observation can be used to obtain a diagnosis, i.e., each of the net transitions appearing as negative or positive peaks in the model difference spectrum can be compared to the unknown spectra and labeled "AD" or "HC". Then each sample diagnosed as either AD or HC, based on the number of AD or HC labels it received.

It should be noted that a slight shift of the wavelengths in the mean AD and mean HC spectra can cause an asymmetry in the difference peak. In this study, we did not use these, and only non-asymmetric emission lines (reported in Table 6) were used to carry out the diagnostic test. Table 6 lists spectral features appearing in the difference spectra and examples of the application of the difference spectrum "majority vote" to two samples, treated as unknowns, i.e., patient 22 (clinical diagnosis: AD) and patient 104 (clinical diagnosis: HC). For patient 22, the number of AD and HC labels was, respectively, 17 and 14. The sample was therefore classified as AD. For patient 104, the number of AD and HC labels was, respectively, 8 and 14, and the sample was therefore classified as HC. It was not possible to assign some emission lines because of the lack of relevant information in the atomic spectra databases.

TABLE 6

| Emitter | Wavelength (nm) | Polarity in model | Patient 22 | Label | Patient 104 | Label |
|---------|----------------|-------------------|------------|-------|-------------|-------|
| Mg II   | 279.5          | +                 | +          | AD    | +           | AD    |
| Mg II   | 280.27         | +                 | +          | AD    | +           | AD    |
| Mg I    | 285.21         | +                 | +          | AD    | +           | AD    |
| —       | 292.35         | +                 | −          | HC    | −           | HC    |
| Na I    | 330.24         | +                 | +          | AD    | +           | AD    |
| Ca II   | 373.69         | −                 | −          | AD    | absent      |       |
| —       | 383.19         | −                 | absent     |       | +           | HC    |
| CN      | 387.08         | +                 | −          | HC    | −           | HC    |
| CN      | 388.29         | +                 | −          | H     | −           | HC    |
| —       | 389.16         | −                 | −          | AD    | +           | HC    |
| —       | 398.25         | +                 | −          | HC    | −           | HC    |
| —       | 401.27         | +                 | −          | HC    | absent      |       |
| —       | 414.01         | −                 | −          | AD    | +           | HC    |
| CN      | 421.52         | +                 | −          | HC    | −           | HC    |
| —       | 431.72         | +                 | −          | HC    | absent      |       |
| —       | 572.15         | −                 | +          | HC    | +           | HC    |
| —       | 572.71         | −                 | +          | HC    | +           | HC    |
| —       | 606.93         | +                 | +          | AD    | −           | HC    |
| —       | 607.48         | +                 | +          | AD    | −           | HC    |
| —       | 617.74         | −                 | −          | AD    | +           | HC    |
| —       | 738.13         | −                 | +          | HC    | absent      |       |
| N I     | 744.33         | −                 | −          | AD    | absent      |       |
| —       | 787.95         | −                 | +          | HC    | +           | HC    |
| Na I    | 818.37         | +                 | +          | AD    | +           | AD    |
| N I     | 818.86         | +                 | +          | AD    | +           | AD    |
| Na I    | 819.48         | +                 | +          | AD    | +           | AD    |
| N I     | 821.63         | +                 | +          | AD    | +           | AD    |
| —       | 852.57         | +                 | +          | AD    | absent      |       |
| —       | 853.79         | +                 | +          | AD    | absent      |       |
| —       | 856.03         | +                 | −          | HC    | absent      |       |
| —       | 881.48         | +                 | −          | HC    | absent      |       |

The spectral assignation of the transitions reported in Table 6, and which are included in the classification analysis, was performed using information available in widely employed databases. In addition, a series of cross-checks were performed.

First, we determined the correlation coefficient between the intensity of each of the transitions appearing in the LIBS spectra: transitions from the same emitter (both in the same ionization stage and in different ionization stages) are typically correlated, which can be used to tentatively identify the emitter even when the databases do not list any transition at the given wavelength. However, the correlation analysis should be considered with caution, because we observed high correlation between different elements (e.g., Mg I 285.21 nm is highly correlated with Na I 589.00 nm and 589.58 nm; H 656.27 nm is highly correlated with O I triplet at 777 nm and with N I transitions at 744.33 nm and 742.36 nm). This suggests that not only the chemical identity of the emitter, but also its origin and sample-specific considerations contribute to the correlation.

Second, LIBS plasmas were considered to be in Local Thermodynamic Equilibrium (LTE) and therefore, based on Boltzmann distribution, high-energy transitions should be less populated than low-energy ones. Therefore, if low-energy transitions of a given element were missing from the spectrum, it was ruled out that some of the other transitions observed in our spectra could be assigned to higher-energy transitions of that same element.

Third, other spectroscopic parameters were included, i.e., Einstein coefficients of spontaneous emission, $A_{ul}$, and relative intensity. With this regard, the possibility of assigning a given peak to a transition with lower $A_{ul}$ was ruled out if other transitions of the same element with higher $A_{ul}$ were not visible in the spectra. Relative intensity was used in a similar way, always taking into account that the latter is only a qualitative indication of the expected intensity of emission peaks.

Based on these considerations, there was no ability to assign with absolute certainty some of the transitions present in the spectra. Tentative assignations are reported for the unassigned transitions reported in Table 6. This is done by relaxing one or more of the constraints described above. For the sake of completeness, for each transition we provide the possible caveats associated with the assignations thus obtained. In the following, we will refer to the lower and upper level involved in the transition as, respectively, $E_1$ and $E_u$.

292.35 nm: this transition does not correlate with any of the other transitions appearing in the spectrum. It may be tentatively assigned it to a high-energy transition of Na II (292.35 nm, $A_{ul}$ 1.41 e+07 $E_1$ 265689.62 cm', $E_u$ 299885.37 cm$^{-1}$). Nonetheless, several Na II transitions between the similar energy levels and higher $A_{ul}$ are not visible in the spectra (e.g., 292.10 nm, 293.77 nm.)

383.16 nm: this transition does not correlate with any of the other transitions appearing in the spectrum. It may be tentatively assigned to a high-energy transition of C II (383.17 nm), though another C II transition at 383.57 nm, with virtually identical spectroscopic parameters and energy levels, is absent from the spectra.

389.16 nm: this transition correlates with only one transition, at 404.81 nm, that we did not use for our analysis. The transition at 404.81 nm may be tentatively assigned to a high-energy transition of O II (404.82 nm, $E_1$ 231427.970 cm$^{-1}$-$E_u$ 256123.231 cm$^{-1}$, no available data for $A_{ul}$). Other O II transitions between lower energy levels and with higher $A_{ul}$ are not visible in the spectra, e.g., 397.33 nm. The transition at 389.16 nm may be tentatively assigned to a high-energy transition of Mg I (389.19 nm, $E_1$ 57833.40 cm$^{-1}$, $E_u$ 83520.47 cm$^{-1}$). Note that a similar Mg I transition at 389.56 nm is absent from the spectra.

398.25 nm: this transition correlates with one CN band at 421.62 nm, one Na I transition at 808.34 nm and one transition at 775.73 nm (the latter, which we did not use for our analysis, may not be assigned to any element, as the only transitions listed in databases at this wavelength are: Ar II 775.70 nm, Nb I 775.73 nm and Rb I 775.76 nm). The 398.25 nm transition may be tentatively assigned to one Ti I transition (398.18 nm, $E_1$ 0-$E_u$ 25102.875 cm$^{-1}$, 4.42 e+07 s$^{-1}$, though other resonance Ti lines with higher $A_{ul}$ are absent from the spectra, e.g., 264.11 nm and 294.20 nm) or one high-energy O II transition (398.27 nm, $E_1$ 189068.514 cm$^{-1}$-$E_u$ 214169.920 cm$^{-1}$, $A_{ul}$ 4.16 e+07 s$^{-1}$, though other O II transitions involving similar energy levels and having higher $A_{ul}$ are not visible in the spectra, e.g., 397.33 nm).

401.27 nm: this transition does not correlate with any of the other transitions appearing in the spectra. It might be tentatively assigned to a high-energy Fe II transition (401.27 nm, $E_1$ 88614.523 cm$^{-1}$-$E_u$ 113 528.091 cm$^{-1}$, no available $A_{ul}$ data). Nonetheless, ground-state and low-energy Fe II transitions with high $A_{ul}$ and relative intensity (respectively in the order of 108 s$^{-1}$ and 105 a.u.) are absent from the spectra.

431.72 nm: this transition does not correlate with any of the other transitions appearing in the spectrum. Three possible candidates for its assignation are high-energy transitions from the following species: O II (431.71 nm, $E_1$ 185235.281 cm$^{-1}$-$E_u$ 208 392.258 cm$^{-1}$, $A_{ul}$ 3.68 e+07 s$^{-1}$), C II (431.73 nm, $E_1$ 186466.02 cm$^{-1}$-$E_u$ 209 622.32 cm$^{-1}$, $A_{ul}$ 5.89 e+07 s$^{-1}$), Ca I (431.71 nm, $E_1$ 47843.760 cm$^{-1}$-$E_u$ 71001.000 cm$^{-1}$, $A_{ul}$ 1.082 e+06 s$^{-1}$).

572.15-572.75 nm: these transitions most likely belong to the same element, based on the observed behavior in spectra and difference spectra, as well as on the fact that they are mutually highly correlated. They are also correlated with three unknown transitions at 741.40, 786.90, 787.94 nm, none of which was included in our analysis. The transition at 572.15 nm may be tentatively assigned to a Na II transition (572.14 nm) for which no data about Einstein coefficient, energy levels or terms is available in either database. No attribution whatsoever could be attempted for the transition at 572.71 nm. In [27], one of the few papers in the LIBS literature about biological samples that features detailed assignation of individual transitions, these peaks were observed and left unassigned.

606.93-607.48 nm: these transitions most likely belong to the same element, based on the observed behavior in spectra and to the fact that they are mutually highly correlated. They are also correlated with one unknown transition at 771.12 nm, that we did not include in our analysis. No attribution could be attempted for either transition.

617.74 nm: this transition does not correlate with any of the other transitions appearing in the spectrum. It might be tentatively assigned to Br I ($E_1$ 75697.05 cm$^{-1}$-$E_u$ 91880.64 cm$^{-1}$, no data for $A_{ul}$ available). Nonetheless, the main Br I peak (827.24 nm, $A_{ul}$ 3.5 e+07, $E_1$ 63436.45 cm$^{-1}$-$E_u$ 75521.50 cm$^{-1}$) is less intense that the 617.74 nm transition.

738.13 nm: this transition correlates with two unknown transitions at 741.40 nm and 786.90 nm, neither of which we used for our analysis. While the transition at 741.40 nm might be tentatively assigned to Cl I ($E_1$ 71958.363 cm$^{-1}$-$E_u$ 85442.430 cm$^{-1}$, $A_{ul}$ 4.7 e+06 s$^{-1}$), the main Cl I lines are either barely visible (837.6 nm, $E_1$ 71958.363 cm$^{-1}$-$E_u$ 83894.037 cm$^{-1}$, $A_{ul}$ 2.8 e+07 s$^{-1}$; 857.53 nm, $E_1$ 72827.038 cm$^{-1}$-$E_u$ 84485.309 cm$^{-1}$, $A_{ul}$ 1.2 e+07 s$^{-1}$) or absent (833.33 nm, $E_1$ 72488.568 cm$^{-1}$-$E_u$ 84485.309 cm$^{-1}$, $A_{ul}$ 1.6 e+07 s$^{-1}$). The 741.40 nm transition was also observed in [1] and left unassigned. The transition at 786.90 nm might be tentatively assigned to a high-energy Fe I transition ($E_1$ 40842.154 cm$^{-1}$-$E_u$ 53545.833 cm$^{-1}$, $A_{ul}$ 105 s$^{-1}$), but main Fe I lines with $E_1$=0 and $A_{ul}$ in the order of 108 s$^{-1}$ are not visible in the spectra (e.g., 252.28 nm and 271.90 nm). The transition at 738.13 nm may be tentatively assigned to a high-energy O II transition ($E_1$ 232745.981 cm 1-$E_u$ 246291.822, no $A_{ul}$ data available, though other O II transitions involving lower energy levels and having $A_{ul}$ in the order of 107 s$^{-1}$ are not visible in the spectra, as mentioned earlier) or to a high-energy, low $A_{ul}$ Fe I transition ($E_1$ 43163.323 cm$^{-1}$-$E_u$ 56707.280 cm$^{-1}$, $A_{ul}$ 5.049 e+05 s$^{-1}$, but main Fe I lines with $E_1$=0 and $A_{ul}$ in the order of 108 s$^{-1}$ are not visible in the spectra, e.g., 252.28 nm and 271.90 nm).

787.95 nm: this transition correlated with the following unknown transitions: 572.15, 572.71 nm; 741.40 nm; 786.90 (the latter was not used in our analysis) whose assignation has been discussed above. The transition at 787.95 nm may be tentatively assigned to a high-energy, low-$A_{ul}$ Fe I transition (787.97 nm, $E_1$ 40594.432 cm$^{-1}$-$E_u$ 53281.689 cm$^{-1}$, $A_{ul}$ 2.185 e+05 s$^{-1}$, but main Fe I lines with $E_1$=0 and $A_{ul}$ in the order of 108 s$^{-1}$ are not visible in the spectra, e.g., 252.28 nm and 271.90 nm).

852.57 nm: this transition does not correlate with any of the other transitions appearing in the spectra. It may be tentatively assigned to a Ca I transition (852.57 nm, $E_1$ 35730.454 cm$^{-1}$-$E_u$ 47456.452 cm$^{-1}$, $A_{ul}$ 1.920 e+06 s$^{-1}$). Transitions between lower energy levels and having $A_{ul}$ in the order of 108 s$^{-1}$, nonetheless, are not visible in the spectra (e.g., 300.086 nm, 551.30 nm).

853.79 nm: this transition does not correlate with any other transition appearing in the spectra. It may be tentatively assigned to a Ca I transition (853.69 nm, $E_1$ 36547.688 cm$^{-1}$-$E_u$ 48258.300 cm$^{-1}$, $A_{ul}$ 1.397 e+05 s$^{-1}$). Transitions between lower energy levels and having $A_{ul}$ in the order of 108 s$^{-1}$, nonetheless, are not visible in the spectra (e.g., 300.086 nm, 551.30 nm).

856.03 nm: this transition correlates with several others, most of which we did not use for our analysis. These are: 678.35 nm (tentative assignation: Fe I 678.33 nm); 773.03 nm (tentative assignation: Ca I 772.97); 775.3 nm (Mg I 775.33 nm); 808.63 nm (Cl I 808.56 nm); 856.63 nm (tentative assignation: N II 856.68 nm); 878.59 nm (no assignment possible); 881.49 nm (see below). For the tentative assignation of all these transitions, the aforementioned caveats should be kept in mind. The 856.03 nm transition may be tentatively assigned to Fe I 855.97 nm ($E_1$ 41178.409 cm$^{-1}$-$E_u$ 52857.800 cm$^{-1}$, $A_{ul}$ 1.261 e+06 s$^{-1}$) but main Fe I lines with $E_1$=0 and $A_{ul}$ in the order of 108 s$^{-1}$ are not visible in the spectra, e.g., 252.28 nm and 271.90 nm.

881.48 nm: this transition correlates with several others, most of which we did not use for our analysis: 421.61 (CN), 518.91 nm (Ca I 518.89 nm), 678.35 nm (tentative assignation: Fe I 678.33 nm); 742.49 nm (N I 742.44 nm); 773.03 nm (tentative assignation: Ca I 772.97 nm); 775.73 nm (tentative assignation: Mg I 775.33 nm); 808.34 nm (tentative assignation: C I 808.38 nm); 808.63 nm (Cl I 808.56 nm); 856.03 nm (see above); 856.63 nm (tentative assignation: N II 856.68 nm); 878.59 nm (no assignation possible). The 881.49 nm transition may be tentatively assigned to a high-energy, low-$A_{ul}$ Ca I transition (881.40 nm, $E_1$ 47456.452 cm$^{-1}$-$E_u$ 58798.920 cm$^{-1}$, $A_{ul}$ 2.082 e+05 s$^{-1}$) or to a very high-energy Fe I transition (881.45 nm, $E_1$ 98114.577 cm$^{-1}$-$E_1$ 109456.381 cm$^{-1}$, $A_{ul}$ 3.0 e+07 s$^{-1}$.) The aforementioned caveats about stronger Ca I and Fe I transitions being absent from the spectra should be kept in mind for what concerns these tentative assignations It was found that not all transitions were visible in the difference spectra of all samples (see Table 6). This stems from the fact that some transitions have similar intensity to that of the mean HC spectrum, resulting in their absence in the difference spectrum. Therefore, due to unavoidable individual differences between the patients, the number of detectable peaks in difference spectra was not always the same. In addition, we observed that not all transitions unequivocally identified patients as either an AD case or a control, and a mix of different labels was the most common occurrence. In such cases, the diagnosis was obtained based on the majority of labels (in this case, AD for patient 22 and HC for patient 104, but we estimated the frequency of such mixed situations, in which the number of AD/HC label may be very similar or even identical. To do this, a parameter was introduced, that was named index of confidence, IC:

$$IC = \frac{\#AD \text{ labels} - \#HC \text{ labels}}{\# \text{ top transitions}} \quad (5)$$

The possible values of this index range between +1 (all top transitions visible in the spectrum difference and providing an AD label) and −1 (all top transitions visible in the spectrum difference and providing an HC label.) IC=0 corresponds to an equal number of AD and HC labels, which would make it impossible to obtain a diagnosis only based on the difference spectrum method.

In this work, there was no situation observed where IC is equal to zero. As this may occur, and to reduce its impact, carrying at least 3 experimental replicas for each patient is advisable. An alternative approach specific to LIBS could be based on performing the difference spectrum test with each single-shot spectrum, rather than with the average spectrum of each patient. However, such an approach is relatively time consuming. It was determined that the frequency of cases with similar numbers of AD and HC labels was 6%, using a threshold values IC<0.1 for AD and IC>−0.1 for HC. These values, with 31 selected spectral features, corresponded to diagnoses obtained with a difference between the number of AD and HC labels less than 3.

The transitions listed in Table 6 were used to diagnose 66 blood plasma samples. It is important to underline that no single spectral transition provided a clear-cut distinction between AD and HC. There was an ability to discriminate between the two classes only by considering all the spectral transitions and the resulting relative numbers of AD vs HC labels. It is also worth mentioning that the samples used to generate the reference difference spectrum were randomly chosen and were selected only with the goal of having a congruous and similar number of AD and HC specimens. The 23 training samples (11 AD and 12 HC) were used, and the resulting model for subsequent analysis of remaining samples was applied.

The cohort of donors analyzed consisted of a sample of patients 50 to 97 years old. We divided this sample set into two separate age groups, one for individuals older than 65 (HC and late-onset AD), and one for individuals younger than 65. The older group had 48 samples and contained a similar number of AD cases and HC (respectively, 26 and 22), while the younger group contained 18 samples, of whom only 2 AD cases and 16 HC samples. Table 7 shows the results, obtained using the same model, of the two separate tests, expressed in terms of total classification accuracy, specificity and sensitivity. These are defined as such:

$$\text{Sensitivity} = \frac{TP}{TP + FN} \times 100 \quad (6)$$

$$\text{Specificity} = \frac{TN}{TN + FP} \times 100 \quad (7)$$

$$\text{Total classification accuracy} = \frac{\# \text{ correct diagnoses}}{\# \text{ samples}} \times 100 \quad (8)$$

where TP=true positive (samples correctly classified as AD), FN=false negative (AD samples wrongly classified as HC), TN=true negative (samples correctly classified as HC), FP=false positive (samples HC samples wrongly classified as AD.)

These data indicate that, while in the younger age group we were unable to distinguish AD and HC, in contrast 31 out of 48 patients were correctly identified in the older age group. This age "gap" in the results can be explained by the fact that the number of AD patients in the younger age group available for this study is very small. As a result, it is not possible to draw any conclusion regarding the impact of the age of the patients on our diagnostics method. For the remainder of this experiment, we therefore focused our investigation on the older age group for which we had more patients and an almost equal number of AD/HC subjects.

TABLE 7

|  | ≤65 years old (2AD, 16 HC) | >65 years old (26 AD, 22 HC) |
| --- | --- | --- |
| Specificity | 47% | 60% |
| Sensitivity | 50% | 68% |
| Total classification accuracy | 50% | 65% |

In this work, the difference spectrum method provided a differentiation between plasma samples from AD and HC subjects in the older age group and also identified salient spectral features that can be used to train a machine learning model/algorithm to classify unknown spectra as AD or healthy.

To improve the classification and investigate the development of an automated minimally invasive method for AD diagnosis, we explored the use of advanced statistical methods available in machine learning algorithms. Due to its simplicity and the fact that it does not require a parameter for optimization, Quadratic Discriminant Analysis (QDA) was selected. This supervised learning technique provides the possibility to account for non-linear decision boundaries between classes. In addition, in QDA, each class is modeled with its own covariance matrix. We tested other statistical methods such as linear discriminant analysis (LDA) and partial least square analysis (PLS) using different type of input data (i.e., raw LIBS spectra vs. spectra resulting from the difference method and by selecting only those features that are either positive or negative in the difference spectra. It was found that QDA with difference spectra as input data and manual feature selection provided the best classification results.

Figure 11:
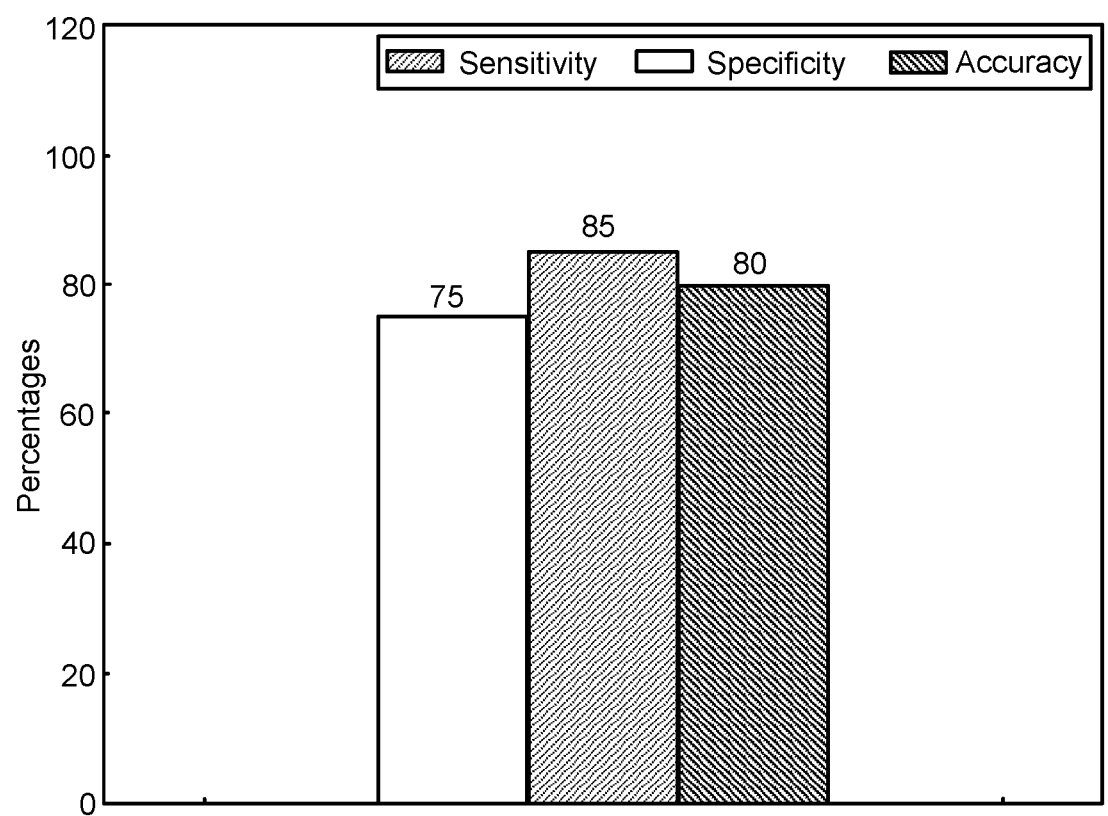
FIG. 11 is a chart illustrating example classification results obtained with supervised learning model trained on manually-selected features determined from difference spectrum measurements.

We used a leave-one-out cross-validation approach, that is, we divided the patients set into a training subset (all patients but one) and a testing subset (the one left-out-patient.) The training set was used to develop a prediction model, which was then used to provide the label of the one left-out patient. This procedure was repeated as many times as we had patients (N), by swapping the subsets, so that eventually each patient was used both in the training set (N−1 times) and as a testing sample (once.) FIG. 11 is a chart illustrating example classification results obtained with supervised learning model trained on manually-selected features determined from difference spectrum measurements and shows the results for classification accuracy, sensitivity and specificity are 80%, 85% and 75% respectively.

For all the tests conducted, sensitivity was higher than specificity, which may indicate that the experimental approach is more appropriate to detect the presence of AD than its absence. This may be rationalized by hypothesizing the existence of a specific spectral profile, possibly of one or more elements, for AD patients, that can be captured by LIBS, either with the difference spectrum method or with statistical approaches. Nonetheless, controls are a group of individuals that do not share this common feature, while at the same time presenting all the individual variability associated to any group of people, which can ultimately contribute to make their identification more difficult.

A feasibility study of LIBS liquid biopsy for the diagnosis of AD was performed, using micro-drops of plasma from AD patients and HC. A data analysis method was developed based on the use of difference spectra as input data for one supervised machine learning algorithm (QDA), which provided classification accuracy, sensitivity and specificity, respectively, of 80%, 85% and 75%. These results were obtained by using selected features from the difference spectra (i.e., all the features that appeared as positive or negative peaks in difference spectra). These results open the way to further investigate and pursue the use of LIBS as a fast and minimally invasive methodology for the diagnosis of AD and possibly better understand its progression. This study contributes to the growing literature focused on investigating the potential of the combined use of LIBS and multivariate statistical approaches to analyze rapidly and relatively simply a large number of biomedical samples for the diagnosis of asymptomatic diseases.

The techniques described herein can be used to diagnose other pathologies in addition to AD. For example, Gulf War Illness (GWI) is a chronic illness with multiple symptoms spanning several domains in individual patients. GWI was first defined by the Centers for Disease Control and Prevention (CDC) after the 1990-1991 Gulf War, but established medical diagnoses, laboratory tests and hypothesis driven research have failed to explain its multi-faceted symptomatology. The etiology of GWI is still unknown and hypotheses involving exposures to vaccines, medications, pesticides, chemical munitions, inhalation of depleted uranium dust and smoke from burn pits and burning oil fields have all been investigated. GWI is reflected in a multi-faceted syndrome with varied presentation in individual patients comprising physical symptoms (fatigue, joint and muscle pain), gastrointestinal disorders, cognitive symptoms, co-morbid syndromes (chronic fatigue syndrome, fibromyalgia, irritable bowel syndrome) and other clinical aspects such as depression and anxiety. Impairment due to GWI can include both cognitive and emotional/behavioral symptoms.

Currently, there are no established biomarkers or other lab tests for diagnosis of GWI or for prediction of the success rate of treatment interventions in patients with GWI symptoms, primarily due to an incomplete understanding of the disease etiology. Several previous studies have searched for GWI diagnostic biomarkers with limited success so far in terms of broader validation of the findings and applicability into clinical practice. The complexity of GWI symptoms suggests implication of multiple pathways with concomitant dysfunction. Together, these aspects of GWI suggest that a global, rather than targeted, approach in diagnostic biomarkers is warranted. Concomitant markers of multiple pathways inhere in intact human-derived biological specimens.

We applied LIBS to study blood plasma from GWI patients and to identify characteristics that distinguish them from non-GWI patients who might share similar symptoms. LIBS can provide a uniquely comprehensive, elemental-level assessment, which can reveal the presence of key, concomitant components in biologic specimens, necessary to correlate with the range of symptoms experienced in GWI.

We analyzed two sets of samples: plasma samples from a cohort of subjects with GWI (GWI pos) and from subjects with chronic low back pain (cLBP) as controls (GWI neg). Patients with cLBP were used as a comparison group (disease control), because they also suffered from a chronic illness and shared some symptoms with GWI but lacked the GWI-associated exposures during deployment, which are believed to play a causative role in GWI. Nine samples from the GWI cohort (GWI pos) and nine samples from the cLBP cohort (GWI neg) were analyzed.

Figure 12:
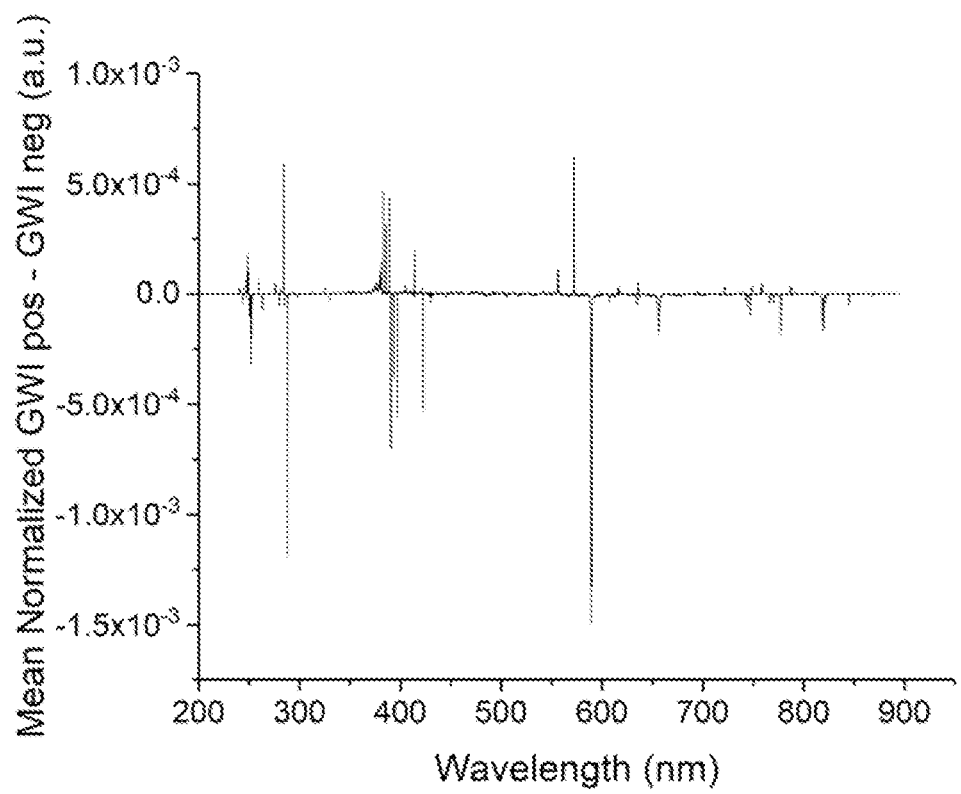
FIG. 12 is a difference spectrum obtained by subtracting the mean normalized GWI neg spectrum (obtained by averaging together all the LIBS spectra of the 4 known GWI neg samples) from the mean normalized GWI pos spectrum (obtained by averaging together all the LIBS spectra of the 4 known GWI pos samples).

To analyze the data, we generated a classification model by using 8 samples of known status (4 GWI pos, 4 GWI neg). We averaged the LIBS spectra of the GWI pos samples, normalized over the total emission intensity, and did the same for the controls, to generate two mean spectra, one for each class. We then subtracted the mean GWI neg spectrum from the mean GWI pos spectrum and obtained a difference spectrum. FIG. 12 is a difference spectrum obtained by subtracting the mean normalized GWI neg spectrum (obtained by averaging together all the LIBS spectra of the 4 known GWI neg samples) from the mean normalized GWI pos spectrum (obtained by averaging together all the LIBS spectra of the 4 known GWI pos samples). This difference spectrum was used to identify the atomic and ionic transitions to include in the classification test, by means of a two-step feature selection procedure.

In a first step of the selection procedure the possibility of spectral interference from the substrate (pure silicon wafer) was mitigated by including in the analysis only the emission peaks that either were completely absent in the spectra of clean silicon or that had intensity lower than 50% of the intensity in the samples' average spectra. This left us with 82 transitions (from about the 200 peaks visible in the spectral range 200-900 nm), that we used to train our model.

To train the model, we employed a leave-one-out cross-validation approach, i.e., we used 7 of the 8 samples with known status as training set, built a model difference spectrum, and tested it with the eighth, left out sample. We then swapped the training and testing subsets, until we built 8 different models and used each to obtain a GWI pos or GWI neg diagnosis for each left-out sample. As described above, this can be done by comparing the polarity of each transition in the test difference spectrum against those in the model. The polarities were determined by simply subtracting the mean normalized GWI neg spectrum from the analogous GWI pos one.

For some transitions, the polarity could not be immediately established with this simple approach, because the difference peaks were asymmetric, most likely due to a slight wavelength shift. In such cases, we determined the intensity of the given peaks in the mean normalized GWI neg spectrum and in the analogous GWI pos by Lorentzian fitting, and we used the difference between the resulting numerical values to determine the polarity of the transition in the difference spectrum. Transitions having the same polarity as the model received a GWI pos label, while those with opposite polarity received a GWI neg label. The diagnosis for each sample was then obtained through a majority vote, i.e., based on the number of GWI pos or GWI neg labels. While we did not observe it in this work, it is possible that samples receive an equal number of GWI pos/GWI neg labels. In such cases, no diagnosis would be possible, and the status of the samples would remain undetermined.

The second step of our feature selection procedure was to identify the transitions that contribute the most to a correct classification of a sample and to rank them based on the percentage of correct labels assigned by each transition to the samples. To establish the number of spectral features providing optimal classification, we repeated the test using various subsets of the 82 features, each corresponding to different percentages of correct diagnoses. To do so, we checked the labels assigned by each transition to each sample, and we tallied the number of correct labels to determine the corresponding percentage of correct diagnoses. We then ranked the transitions based on this percentage, and ran separate tests using different thresholds, which results are reported in Table 8. In this Table, for example, Threshold>70% indicates that the specific test was run using only the transitions that provided more than 70% correct labels. The results shown in Table 8 are expressed in terms of the classification metrics of equations (6), (7), and (8). "N=82" indicates results that were obtained using all the spectral features that were visible in the sample spectra, but absent in the substrate (N=82). The remaining columns in the table indicate three different thresholds used to select the most diagnostic features, i.e., results obtained using only the transitions providing at least 60% (N=32), 70% (N=17), and 80% (N=3) of correct diagnoses.

TABLE 8

| Classification metrics (Training Set) | Results with different subsets of transitions | | | |
|---|---|---|---|---|
| | N = 82 | N = 32 | N = 17 | N = 3 |
| Classification accuracy (%) | 75 | 75 | 87.5 | 87.5 |
| Sensitivity (%) | 100 | 100 | 100 | 100 |
| Specificity (%) | 50 | 50 | 75 | 75 |

When using all the selected transitions, 2 of the control samples are misclassified as GWI pos (false positives) but using a threshold of at least 70% correct diagnoses (N=17) brought the number of misclassified samples to only one. Since changing the threshold to 80% correct diagnoses (N=3) did not improve the results, we selected 70% as the optimal threshold for the blind test, so to minimize the risk of overfitting the cross-validation data set.

These 17 top transitions are listed in Table 9. While several could not be assigned with certainty, and were therefore left blank, Table 9 shows that some of the elements contributing the most to the classification accuracy are alkaline metals (Na, K) and Fe.

TABLE 9

| Wavelength (nm) | Emitter | % Correct diagnoses (cross validation) |
|---|---|---|
| 606.97 | — | 87.5 |
| 818.33 | Na I | 87.5 |
| 819.48 | Na I | 87.5 |
| 276.43 | — | 75.0 |
| 275.63 | Fe I | 75.0 |
| 556.25 | — | 75.0 |
| 281.21 | — | 75.0 |
| 758.73 | — | 75.0 |
| 324.91 | — | 75.0 |
| 330.27 | Na I | 75.0 |
| 556.80 | — | 75.0 |
| 769.90 | K I | 75.0 |
| 589.00 | Na I | 75.0 |
| 380.98 | — | 75.0 |
| 379.80 | — | 75.0 |
| 244.77 | Fe I | 75.0 |
| 589.59 | Na I | 75.0 |

The blind test was carried out with 10 additional samples, using the 17 top ranked transitions reported in Table 9. The difference spectra for the unknown samples were obtained by subtracting the normalized mean spectrum of the 4 known GWI neg specimens from the normalized spectra of each unknown sample, and the resulting polarities compared to those of the model difference spectrum comprised of all eight known specimens. The results obtained after breaking the blind are reported in Table 10, where "Threshold>70%" indicates that the results were obtained using only the N=17 spectral features that provided at least 70% correct diagnoses in the cross-validation test. As previously seen for the cross-validation set, also in this group of samples there was only one misclassification, and it was a false positive.

TABLE 10

| Classification metrics (Blind Test) | Results with N = 17 top transitions (threshold >70%) |
|---|---|
| Classification accuracy (%) | 90.0 |
| Sensitivity (%) | 100 |
| Specificity (%) | 83.3 |

This work is the first example of the application of an optical spectroscopy technique, LIBS, to the diagnosis of GWI in Veterans. No known biomarkers have so far been validated for GWI, and as a result there is an urgent need for the development of an untargeted and unbiased method to distinguish GWI-positive patients. We adopted a liquid biopsy approach, a minimally invasive approach based on analyzing microliter droplets of blood plasma specimens from two groups, those with and without GWI, after depositing and drying the specimens on solid substrates. For this work, we used the difference spectrum method to provide a multivariate analysis approach. This method is based on generating a model difference spectrum with samples of known status and comparing the transitions' polarities with those of the unknown samples' difference spectra to obtain a diagnosis. In this work, we used 8 samples of known status (4 GWI pos, 4 GWI neg) to cross-validate our method, identify the most diagnostic transitions, and set a threshold for the optimal number of spectral features to be used for the blind test. In the cross-validation results, only one sample was not correctly identified, and it was a false positive for GWI. It is possible to explain this by the fact that, while GWI is twice as prevalent in deployed veterans, it has also been described in 15% of non-deployed veterans.

To further test the validity of our approach, we performed a blind test using 10 additional samples, whose status was unknown to the researchers performing the LIBS measurements and analysis. The results obtained after breaking the blind were impressive. We achieved a classification accuracy 90.0%; sensitivity 100%; specificity 83.3%. These results demonstrate that, despite the limited number of specimens that were available for this first study, LIBS shows a clear potential for minimally invasive GWI diagnosis.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

While certain features of the described implementations have been illustrated as described herein, many modifications, substitutions, changes and equivalents will now occur to those skilled in the art. It is, therefore, to be understood that the appended claims are intended to cover all such modifications and changes as fall within the true spirit of the various embodiments.

What is claimed is:

1. A method for screening patients with, diagnosing, or monitoring progress of a pathology using laser induced breakdown spectroscopy (LIBS) and biological fluids, the method comprising:

focusing light from a laser light source on a sample of biological fluid deposited on a substrate, wherein an energy and pulse length of the light focused on the sample cause ablation of the sample and formation of a plasma;

collecting optical emission from the plasma;

providing the collected optical emission to a spectroscopic acquisition component, wherein the spectroscopic acquisition component provides information on spectral data of the plasma;

providing the spectral data from the collected optical emission to a processing component, wherein the processing component includes one or more processors; and using a machine learning algorithm and the one or more processors to screen a patient with, diagnose, or monitor progress of the pathology in the sample, wherein the machine learning algorithm is trained on a training set that includes spectral features in a difference spectrum derived from differences between a first LIBS optical emission spectrum collected from one or more samples of the biological fluid that have the pathology or known progress of the pathology and a second LIBS optical emission spectrum collected from one or more samples of the biological fluid that do not have the pathology or the known progress of the pathology, wherein using the machine learning algorithm and the one or more processors to screen a patient with the pathology, diagnose the pathology, or monitor progress of the pathology in the sample includes determining polarities of spectral features in the spectral data of the plasma when compared to a model difference spectrum and classifying the sample based on the number of positive polarity spectral features in the spectral data of the plasma compared to the number of negative polarity spectral features in the spectral data of the plasma.

2. The method of claim 1, wherein the biological fluid includes blood or blood plasma and wherein the pathology is Alzheimer's disease.

3. The method of claim 1, wherein the machine learning algorithm includes a Quadratic Discriminant Analysis (QDA) algorithm.

4. The method of claim 1, wherein the spectral features used to train the machine learning algorithm are weighted based on their ability to correctly classify a sample.

5. The method of claim 1, wherein each spectral feature in the spectral data of the plasma used in the machine learning algorithm and the one or more processors to screen a patient with the pathology, diagnose the pathology, or monitor progress of the pathology in the sample is labelled as indicating or contra-indicating the pathology or the known progress of the pathology based on its polarity in the difference spectrum.

6. The method of claim 5, wherein the first LIBS optical emission spectrum and second LIBS optical emission spectrum are normalized for their total emission intensities.

7. The method of claim 5, wherein spectral features used in the machine learning algorithm and the one or more processors to screen a patient with the pathology, diagnose the pathology, or monitor progress of the pathology in the sample include only features that are absent in a spectrum of the substrate.

8. The method of claim 5, wherein spectral features used in the machine learning algorithm and the one or more processors to screen a patient with the pathology, diagnose the pathology, or monitor progress of the pathology in the sample include only features that are absent in a spectrum of the substrate or that, in a spectrum of the substrate, had an intensity lower than 50% of an average intensity in the LIBS optical emission spectra from multiple GWI positive samples.

9. The method of claim 1, wherein providing the spectral data from the collected optical emission to the processing component includes generating difference spectra to enhance spectral differences between samples obtained from patients having the pathology and samples obtained from healthy controls.

10. A system for screening patients with, diagnosing, or monitoring progress of a pathology using laser induced breakdown spectroscopy (LIBS) and biological fluids, using laser induced breakdown spectroscopy (LIBS) and biomedical fluids, the system comprising:
   a substrate configured to support a sample of a biological fluid;
   a laser light source;
   an optical subsystem configured to receive light from the laser light source and focus the received light on the sample on the substrate, wherein an energy and a pulse length of the laser light source are configured to cause ablation of the sample and substrate and formation of a plasma;
   a light collection optical subsystem configured to collect optical emission from the plasma;
   a spectroscopic acquisition component configured to receive collected optical emission from the light collection optical subsystem and to provide spectral data, the spectroscopic acquisition component including a spectrometer and a detector; and
   a processing component including one or more processors and configured to receive the spectral data from the spectroscopic acquisition component, wherein the one or more processors are configured use a machine learning algorithm to screen a patient with, diagnose, or monitor progress of the pathology in the sample, wherein the machine learning algorithm is trained on a training set that includes spectral features in a difference spectrum derived from differences between a first LIBS optical emission spectrum collected from one or more samples of the biological fluid that have the pathology or known progress of the pathology and a second LIBS optical emission spectrum collected from one or more samples of the biological fluid that do not have the pathology or the known progress of the pathology,
   wherein using the machine learning algorithm and the one or more processors to screen a patient with the pathology, diagnose the pathology, or monitor progress of the pathology in the sample includes determining polarities of spectral features in the spectral data of the plasma when compared to a model difference spectrum and classifying the sample based on the number of positive polarity spectral features in the spectral data of the plasma compared to the number of negative polarity spectral features in the spectral data of the plasma.

11. The system of claim 10, wherein the biological fluid includes blood or blood plasma and the pathology is Alzheimer's disease.

12. The system of claim 10, wherein the machine learning algorithm includes a Quadratic Discriminant Analysis (QDA) algorithm.

13. The system of claim 10, wherein the spectral features used to train the machine learning algorithm are weighted based on their ability to correctly classify a sample.

14. The system of claim 10, wherein each spectral feature in the spectral data of the plasma used in the machine learning algorithm and the one or more processors to screen a patient with the pathology, diagnose the pathology, or monitor progress of the pathology in the sample is labelled as indicating or contra-indicating the pathology or the known progress of the pathology based on its polarity in the difference spectrum.

15. The system of claim 14, wherein the first LIBS optical emission spectrum and second LIBS optical emission spectrum are normalized for their total emission intensities.

16. The system of claim 14, wherein spectral features used in the machine learning algorithm and the one or more processors to screen a patient with the pathology, diagnose the pathology, or monitor progress of the pathology in the sample include only features that are absent in a spectrum of the substrate.

17. The system of claim 14, wherein spectral features used in the machine learning algorithm and the one or more processors to screen a patient with the pathology, diagnose the pathology, or monitor progress of the pathology in the sample include only features that are absent in a spectrum of the substrate or that, in a spectrum of the substrate, had an intensity lower than 50% of an average intensity in the LIBS optical emission spectra from multiple GWI positive samples.

18. The system of claim 10, wherein providing the spectral data from the collected optical emission to the processing component includes generating difference spectra to enhance spectral differences between samples obtained from patients having the pathology and samples obtained from healthy controls.

* * * * *